US012608982B2

(12) United States Patent
Schueren et al.

(10) Patent No.: US 12,608,982 B2
(45) Date of Patent: Apr. 21, 2026

(54) SYSTEMS AND METHODS FOR BIOMETRIC DATA COLLECTIONS

(71) Applicant: IntegenX Inc., Pleasanton, CA (US)

(72) Inventors: Robert A. Schueren, Los Altos Hills, CA (US); David King, Menlo Park, CA (US); Chungsoo Charles Park, Redwood City, CA (US); Stevan B. Jovanovich, Livermore, CA (US)

(73) Assignee: IntegenX Inc., Pleasanton, CA (US)

( * ) Notice: Subject to any disclaimer, the term of this patent is extended or adjusted under 35 U.S.C. 154(b) by 591 days.

(21) Appl. No.: 17/972,102

(22) Filed: Oct. 24, 2022

(65) Prior Publication Data

US 2023/0119468 A1     Apr. 20, 2023

Related U.S. Application Data

(63) Continuation of application No. 16/234,385, filed on Dec. 27, 2018, now Pat. No. 11,482,052, which is a (Continued)

(51) Int. Cl.
| | |
|---|---|
| *G06V 40/70* | (2022.01) |
| *G06V 40/10* | (2022.01) |

(Continued)

(52) U.S. Cl.
CPC .............. *G06V 40/70* (2022.01); *G06V 40/10* (2022.01); *G06V 40/67* (2022.01); *G10L 17/00* (2013.01);

(Continued)

(58) Field of Classification Search
CPC ........... G06K 9/00892; G06K 9/00912; G06K 9/00604; G06K 9/0004; G06K 9/00255;

(Continued)

(56) References Cited

U.S. PATENT DOCUMENTS

| | | | |
|---|---|---|---|
| 5,364,596 | A | 11/1994 | Magnussen, Jr. |
| 5,957,167 | A | 9/1999 | Feygin |

(Continued)

FOREIGN PATENT DOCUMENTS

| | | |
|---|---|---|
| CN | 201087836 | 7/2008 |
| CN | 101918821 A | 12/2010 |

(Continued)

OTHER PUBLICATIONS

DE 201 16 511 U1 (MWG Biotech) Feb. 20, 2003 (Feb. 20, 2003) entire document cited in International Search Report PCT/US2012/057130 dated Nov. 28, 2012.

(Continued)

*Primary Examiner* — Nancy Bitar
(74) *Attorney, Agent, or Firm* — Jones Burke, PLLC

(57) ABSTRACT

A system comprises an authentication sub-system configured to authenticate a user and a biochemical analysis sub-system configured to perform a biochemical analysis on a biological sample provided to the biochemical analysis sub-system. The system is configured to authenticate a user using the authentication sub-system, instruct an authenticated user to provide a biological sample to the biochemical analysis sub-system, execute a biochemical analysis on a provided biological sample.

19 Claims, 25 Drawing Sheets

Related U.S. Application Data continuation of application No. 14/919,741, filed on Oct. 22, 2015, now Pat. No. 10,210,410.

(60) Provisional application No. 62/067,429, filed on Oct. 22, 2014.

(51) Int. Cl.

| | |
|---|---|
| *G06V 40/60* | (2022.01) |
| *G10L 17/00* | (2013.01) |
| *G16B 50/00* | (2019.01) |
| *G16B 50/30* | (2019.01) |
| *G16B 99/00* | (2019.01) |
| *G16H 10/40* | (2018.01) |
| *G16H 40/63* | (2018.01) |

(52) U.S. Cl.

CPC ............. *G16B 50/00* (2019.02); *G16B 50/30* (2019.02); *G16B 99/00* (2019.02); *G16H 10/40* (2018.01); *G16H 40/63* (2018.01); *G06F 2218/00* (2023.01); *G06V 40/15* (2022.01)

(58) Field of Classification Search

CPC .......... G06K 2009/00946; G06K 2009/00939; G10L 17/005; H04W 84/12

USPC ........................................................ 382/116

See application file for complete search history.

(56) References Cited

U.S. PATENT DOCUMENTS

| | | | |
|---|---|---|---|
| 6,672,344 | B1 | 1/2004 | Stokes |
| 7,046,357 | B2 | 5/2006 | Weinberger |
| 7,130,375 | B1 | 10/2006 | Yun |
| 7,400,704 | B1 | 7/2008 | Yun et al. |
| 7,445,926 | B2 | 11/2008 | Mathies et al. |
| 7,657,001 | B2 | 2/2010 | Van De Haar |
| 7,729,471 | B2 | 6/2010 | Burdett, Jr. et al. |
| 8,837,678 | B2 | 9/2014 | Turqueti et al. |
| D772,086 | S | 11/2016 | Schueren |
| 10,210,410 | B2 | 2/2019 | Schueren et al. |
| 11,482,052 | B2 | 10/2022 | Schueren et al. |
| 11,797,020 | B1* | 10/2023 | Jiang ........................ G06T 7/74 |
| 11,810,345 | B1* | 11/2023 | Gayaka ................ G06V 40/161 |
| 12,145,626 | B1* | 11/2024 | Gayaka ............. B60W 60/0027 |
| 2002/0045189 | A1* | 4/2002 | Imajo ....................... C07K 7/02 |
| | | | 435/7.1 |
| 2002/0113707 | A1 | 8/2002 | Grunes |
| 2002/0187560 | A1 | 12/2002 | Pezzuto |
| 2003/0187359 | A1* | 10/2003 | Njemanze ............ A61B 5/7253 |
| | | | 600/454 |
| 2004/0018491 | A1 | 1/2004 | Gunderson |
| 2004/0021068 | A1 | 2/2004 | Staats |
| 2004/0022676 | A1 | 2/2004 | Hamilton |
| 2004/0146433 | A1 | 7/2004 | Massaro |
| 2004/0151349 | A1* | 8/2004 | Milne, III ............ G06V 40/172 |
| | | | 382/181 |
| 2004/0209354 | A1 | 10/2004 | Mathies et al. |
| 2005/0026300 | A1 | 2/2005 | Samper |
| 2005/0053952 | A1 | 3/2005 | Hong |
| 2005/0161669 | A1 | 7/2005 | Jovanovich |
| 2005/0241941 | A1 | 11/2005 | Parce |
| 2005/0266582 | A1 | 12/2005 | Modlin |
| 2007/0015179 | A1 | 1/2007 | Klapperich |
| 2007/0034025 | A1 | 2/2007 | Pant |
| 2007/0175756 | A1 | 8/2007 | Nguyen |
| 2007/0204497 | A1* | 9/2007 | de la Huerga ........... B65C 9/46 |
| | | | 283/67 |
| 2007/0208534 | A1 | 9/2007 | Benfield |
| 2007/0237686 | A1 | 10/2007 | Mathies |
| 2007/0263049 | A1 | 11/2007 | Preckel |
| 2007/0286342 | A1 | 12/2007 | Fuller |
| 2008/0014576 | A1 | 1/2008 | Jovanovich |
| 2008/0014589 | A1 | 1/2008 | Link |
| 2008/0027756 | A1 | 1/2008 | Gabriel |
| 2008/0164155 | A1 | 7/2008 | Pease |
| 2008/0257437 | A1 | 10/2008 | Fernandes |
| 2008/0281090 | A1 | 11/2008 | Lee |
| 2008/0307117 | A1 | 12/2008 | Muller-Cohn |
| 2009/0060138 | A1 | 3/2009 | Van De Haar |
| 2009/0141867 | A1 | 6/2009 | Burdett, Jr. |
| 2009/0155123 | A1* | 6/2009 | Williams ................ B01L 3/021 |
| | | | 422/65 |
| 2009/0178934 | A1 | 7/2009 | Jarvius |
| 2009/0275038 | A1 | 11/2009 | Hodge |
| 2010/0005932 | A1 | 1/2010 | Young |
| 2010/0120098 | A1 | 5/2010 | Grunenwald |
| 2010/0165784 | A1 | 7/2010 | Jovanovich |
| 2010/0265068 | A1 | 10/2010 | Brackmann |
| 2010/0285578 | A1 | 11/2010 | Selden |
| 2010/0303687 | A1 | 12/2010 | Blaga |
| 2011/0067098 | A1 | 3/2011 | Nelson |
| 2011/0207140 | A1 | 8/2011 | Handique |
| 2012/0271094 | A1 | 10/2012 | Fuller |
| 2012/0322666 | A1 | 12/2012 | Pham |
| 2013/0039474 | A1 | 2/2013 | Turqueti |
| 2013/0131994 | A1 | 5/2013 | Birdwell |
| 2013/0139895 | A1 | 6/2013 | Vangbo |
| 2013/0202182 | A1 | 8/2013 | Rowe |
| 2013/0215116 | A1 | 8/2013 | Siddique |
| 2013/0336545 | A1 | 12/2013 | Pritikin |
| 2014/0065628 | A1 | 3/2014 | Van Gelder |
| 2014/0073043 | A1 | 3/2014 | Holmes |
| 2014/0081657 | A1* | 3/2014 | Neuvonen ............... G16Z 99/00 |
| | | | 705/3 |
| 2015/0025915 | A1 | 1/2015 | Lekas |
| 2015/0078552 | A1 | 3/2015 | Perlin |
| 2015/0088772 | A1 | 3/2015 | Shwartz |
| 2015/0121522 | A1 | 4/2015 | Guido |
| 2015/0136604 | A1 | 5/2015 | Nielsen |
| 2016/0116439 | A1 | 4/2016 | Kindwall |
| 2016/0274042 | A1 | 9/2016 | Chen |
| 2016/0367981 | A1 | 12/2016 | Wunderle |
| 2017/0109593 | A1 | 4/2017 | Schueren |
| 2018/0262557 | A1 | 9/2018 | Schueren |
| 2018/0293680 | A1 | 10/2018 | Schueren et al. |

FOREIGN PATENT DOCUMENTS

| | | | |
|---|---|---|---|
| CN | 101304689 | B | 3/2012 |
| CN | 101918821 | B | 5/2012 |
| DE | 20116511 | U1 | 2/2003 |
| EP | 1948020 | A2 | 7/2008 |
| EP | 2223091 | A1 | 9/2010 |
| JP | 2009514636 | A | 4/2009 |
| JP | 2011505563 | A | 2/2011 |
| JP | 2014028281 | A | 2/2014 |
| JP | 5451630 | B2 | 3/2014 |
| RU | 2010126726 | A | 1/2012 |
| RU | 2479836 | C2 | 4/2013 |
| WO | 2004061085 | A2 | 7/2004 |
| WO | 2005072858 | A1 | 8/2005 |
| WO | 2006032044 | A2 | 3/2006 |
| WO | 2007054893 | A2 | 5/2007 |
| WO | 2007082480 | A1 | 7/2007 |
| WO | 2008030631 | | 3/2008 |
| WO | 2008039875 | A1 | 4/2008 |
| WO | 2008115626 | A2 | 9/2008 |
| WO | 2009073499 | A1 | 6/2009 |
| WO | 2009108260 | A2 | 9/2009 |
| WO | 2010077322 | | 7/2010 |
| WO | 2010121326 | A1 | 10/2010 |
| WO | 2010141921 | A1 | 12/2010 |
| WO | 2011011172 | A1 | 1/2011 |
| WO | 2011068762 | A1 | 6/2011 |
| WO | 2011094577 | A2 | 8/2011 |
| WO | 2011123801 | A1 | 10/2011 |
| WO | 2011150232 | A2 | 12/2011 |
| WO | 2012024657 | A1 | 2/2012 |
| WO | 2012024658 | A2 | 2/2012 |
| WO | 2013028643 | A1 | 2/2013 |
| WO | 2013049071 | A1 | 4/2013 |

(56) References Cited

FOREIGN PATENT DOCUMENTS

| | | | |
|---|---|---|---|
| WO | 2013059750 | A1 | 4/2013 |
| WO | 2013130910 | A1 | 9/2013 |
| WO | 2015073999 | A1 | 5/2015 |
| WO | 2015179098 | A1 | 11/2015 |
| WO | 2016176671 | A2 | 11/2016 |
| WO | 2017053462 | A1 | 3/2017 |
| WO | 2017059356 | A1 | 4/2017 |
| WO | 2017069856 | A1 | 4/2017 |

OTHER PUBLICATIONS

Extended European Search Report dated Aug. 16, 2018 issued in Application No. EP 16787296.9.

Figarelli, Vince, "The Arizona DPS Rapid DNA Program," [SLIDES] Aug. 31, 2014, XP055497564, pp. 1-46. [retrieved on Aug. 6, 2018] <URL:https://integenx.comjwp-contentjupload sj2014/08/Figarelli-ASCLD-Rapid-DNA_2014.pdf>.

Final Office Action dated Feb. 28, 2018 issued in U.S. Appl. No. 14/919,741.

Integenx, [Internet Article] "Announces First State-Wide deployment of the RapidHIT System with SmallPond™ at Arizona Department of Public Safety" Cases, Press Release, May 14, 2014. [retrieved on Aug. 6, 2018] <URL:https://ntegenx.comjintegenx-announce s-first-state-wide-deployment-of-the-rapid hit-system-with-smallpond-at-arizona-department-of-public-safety/> figures 1-3.

International Preliminary Report on Patentability dated Apr. 12, 2018 issued in Application No. PCT/US2016/054994.

International Preliminary Report on Patentability dated Apr. 5, 2018 issued in Application No. PCT/US2016/052930.

International Preliminary Report on Patentability dated May 3, 2018 issued in Application No. PCT/US2016/050003.

International Preliminary Report on Patentability dated Nov. 9, 2017 issued in Application No. PCT/US2016/030331.

International Search Report and Written Opinion dated Jan. 12, 2017 issued in Application No. PCT/US16/50003.

International Search Report and Written Opinion dated Jan. 19, 2017 issued in Application No. PCT/US16/54994.

International Search Report and Written Opinion dated Oct. 28, 2016 issued in Application No. PCT/US16/30331.

International Search Report dated Dec. 9, 2016 issued in Application No. PCT/US16/52930.

International Search Report PCT/ US 10/37545 dated Sep. 28, 2010 cited in parent case U.S. Appl. No. 14/919,741.

International Search Report PCT/US 10/58227 dated Mar. 3, 2011 cited in parent case U.S. Appl. No. 14/919,741.

International Search Report PCT/US 11/30973 dated May 26, 2011 cited in parent case U.S. Appl. No. 14/919,741.

International Search Report PCT/US 11/48527 dated Dec. 19, 2011 cited in parent case U.S. Appl. No. 14/919,741.

International Search Report PCT/US 12/51632 dated Oct. 10, 2012 cited in parent case U.S. Appl. No. 14/919,741.

International Search Report PCT/US 12/61223 dated Feb. 15, 2013 cited in parent case U.S. Appl. No. 14/919,741.

International Search Report PCT/US 15/28510 dated Sep. 29, 2015 cited in parent case U.S. Appl. No. 14/919,741.

International Search Report PCT/US2010/040490 dated Aug. 13, 2010 cited in parent case U.S. Appl. No. 14/919,741.

International Search Report PCT/US2012/057130 dated Nov. 28, 2012 cited in parent case U.S. Appl. No. 14/919,741.

International Search Report PCT/US2013/028462 dated Jul. 5, 2013 cited in parent case U.S. Appl. No. 14/919,741.

International Search Report PCT/US2014/064927 dated Feb. 11, 2015 cited in parent case U.S. Appl. No. 14/919,741.

Notice of Allowance dated Sep. 21, 2018 issued in U.S. Appl. No. 14/919,741.

U.S. Appl. No. 15/761,066, filed Mar. 16, 2018, King et al.

Wikipedia: "Extract, transform, load" [Internet Article] Apr. 25, 2015. XP055497574., pp. 1-10. [retrieved on Aug. 6, 2018] <URL:https:jjen.wikipedia.orgjwjindex.php?title=Extract. transform. load&oldid=659213 002>.

Wikipedia: "Mobile Web," [Internet Article] Mar. 27, 2015, XP055497568, pp. 1-5. [retrieved on Aug. 6, 2018] URL:https:jjen. wikipedia.orgjwjindex.php?title=Mobile Web&oldid=653815098>.

Wikipedia: "Unified communications," [Internet Article] Apr. 16, 2015, XP055497572., pp. 1-5. [retrieved on Aug. 6, 2018] <URL:https:jjen.wikipedia.orgjwjindex.php?title=Unified communications&oldid=65672652 0>.

U.S. Appl. No. 15/570,730, filed Oct. 30, 2017, Schueren et al.

U.S. Appl. No. 15/910,743, filed Mar. 2, 2018, Schueren et al.

* cited by examiner

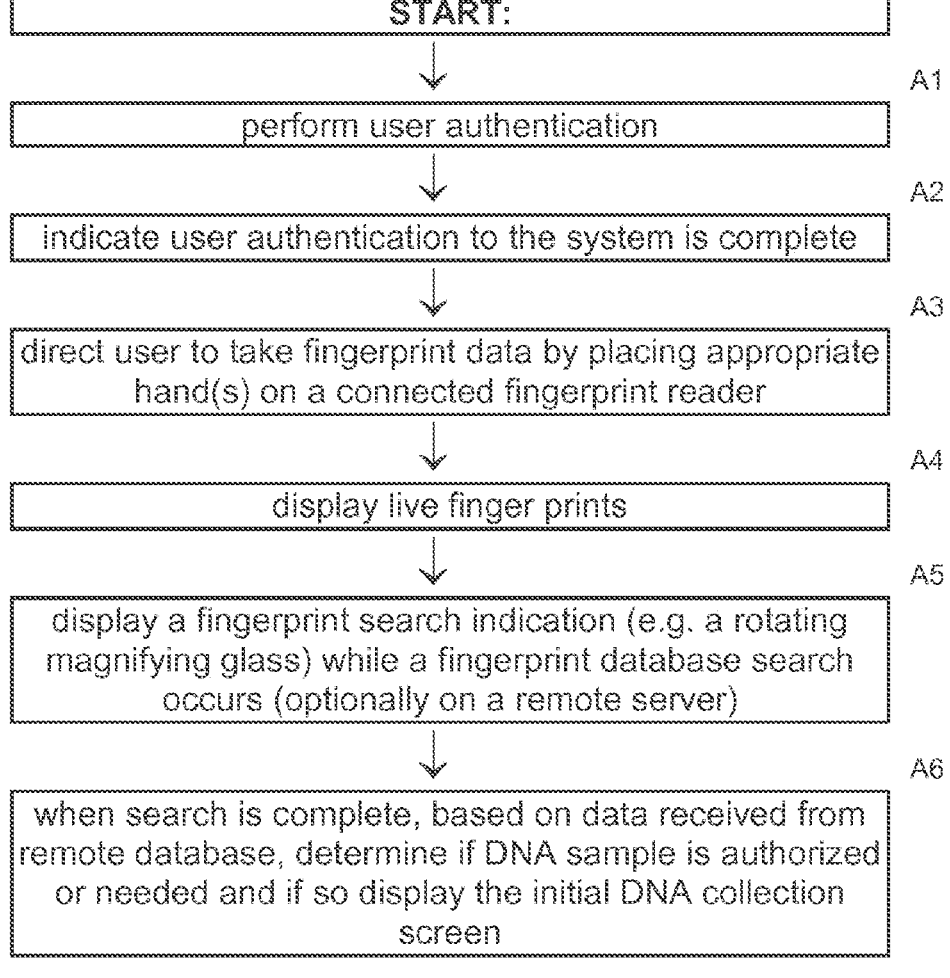

START:

perform user authentication — A1 indicate user authentication to the system is complete — A2 direct user to take fingerprint data by placing appropriate hand(s) on a connected fingerprint reader — A3 display live finger prints — A4 display a fingerprint search indication (e.g. a rotating magnifying glass) while a fingerprint database search occurs (optionally on a remote server) — A5 when search is complete, based on data received from remote database, determine if DNA sample is authorized or needed and if so display the initial DNA collection screen — A6

*FIG. 1A*

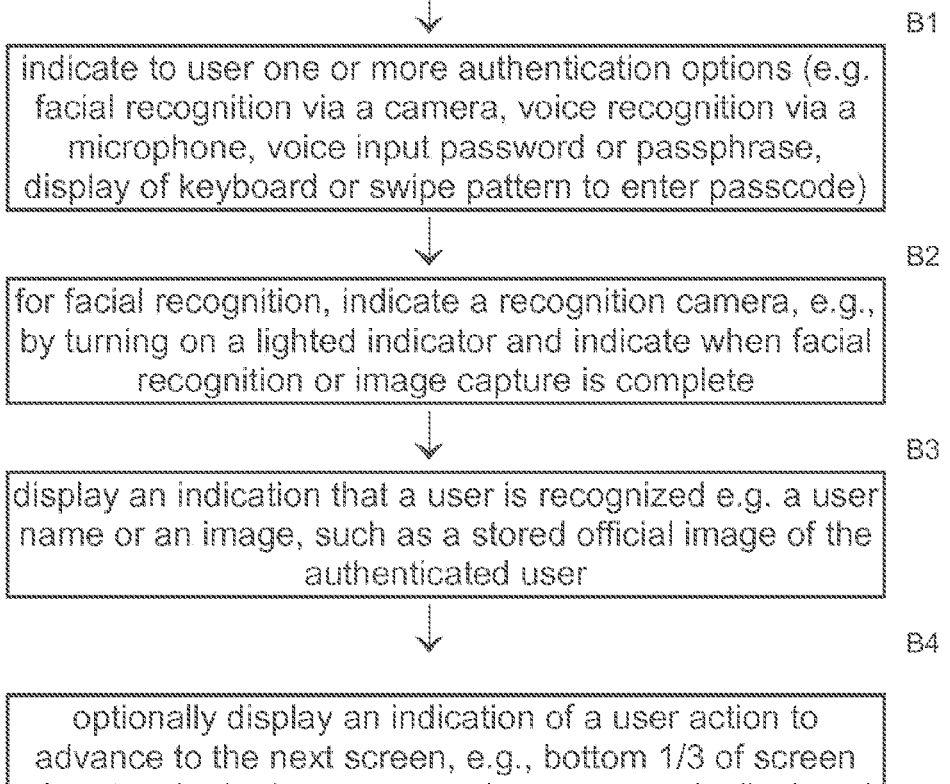

B1 indicate to user one or more authentication options (e.g. facial recognition via a camera, voice recognition via a microphone, voice input password or passphrase, display of keyboard or swipe pattern to enter passcode)

B2 for facial recognition, indicate a recognition camera, e.g., by turning on a lighted indicator and indicate when facial recognition or image capture is complete

B3 display an indication that a user is recognized e.g. a user name or an image, such as a stored official image of the authenticated user

B4 optionally display an indication of a user action to advance to the next screen, e.g., bottom 1/3 of screen when touched advances or an icon or arrow is displayed

*FIG. 1C*

How to change cartridge.

.

.

Step by step instructions including text, figures, and/or videos are shown on one or more screens

SYSTEMS AND METHODS FOR BIOMETRIC DATA COLLECTIONS

CROSS REFERENCE TO RELATED APPLICATIONS

This application is a continuation application of U.S. patent application Ser. No. 16/234,385, filed Dec. 27, 2018, which is a continuation application of U.S. patent application Ser. No. 14/919,741 filed on Oct. 22, 2015 (now U.S. Pat. No. 10,210,410), which claims priority from U.S. provisional patent application 62/067,429 filed on Oct. 22, 2014.

This application is related to the following applications assigned to IntegenX Inc.: U.S. provisional application Ser. No. 62/067,404 entitled "Systems And Methods For Sample Preparation, Processing And Analysis" (Kindwall, et al.), filed Oct. 22, 2014; and U.S. provisional application Ser. No. 62/067,120 entitled "Fluidic Cartridge With Valve Mechanism" (Eberhart, et al.), filed Oct. 22, 2014.

Each of these applications are incorporated herein by reference in their entirety. Furthermore, all referenced documents and applications herein and all documents referenced therein are incorporated herein by reference for all purposes. This application may be related to other patent applications and issued patents assigned to the assignee indicated above. These applications and issued patents are incorporated herein by reference to the extent allowed under applicable law.

COPYRIGHT NOTICE

TECHNICAL FIELD

The present invention relates to logic systems. More particularly, it relates to control systems, computer systems and associated systems and methods that facilitate the collection, processing, analysis and/or validation of biometric data. In further embodiments, one or more methods may be implemented on a data handling device or system, such as a computer or other information enabled device. In further embodiments, methods and/or systems for performing one or more analysis over a communication network are provided. In further embodiments, the invention relates to integrated automated fingerprint identifications systems.

BACKGROUND

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

SUMMARY

According to specific embodiments, methods and/or systems and/or devices are described that can be used together or independently to provide improved collection, processing, analysis, and/or validation of biometric data and optionally related data at a processing location. In specific embodiments, methods and/or systems and/or devices facilitate and/or direct workflow to allow non-technical users to collect and validate electronically captured biometric data (e.g., fingerprints, photographs, voice-prints, retinal-scans, etc.), biochemical biometric data (e.g., DNA or protein or other chemically analyzable data) and related data (name, address, identification numbers, etc.). In further embodiments, a system or method is described that provides improved interaction between a biometric data collection and processing system and one or more server systems or databases (e.g., generally remote systems accessible over the Internet or other networks, e.g., central crime registry database, identification databases, etc.). In specific embodiments, novel systems and methods for user interaction with a biometric data collection system are provided. In other embodiments, novel systems and methods for biometric data collection and biological sample collecting and analysis are provided.

One system according to specific embodiments, referred at times herein as the "Rapid DNA analyzer" can, among other features, provide workflow improvement for collection of biometric data generated by an analysis done by the system (e.g., DNA analysis data by electrophoresis) along with collection and verification of integrated captured biometric data (e.g., fingerprints, photographs, retinal scans, voice prints, etc.)

According to specific embodiments, a system (e.g., a Rapid DNA analyzer) can be used to capture prints (e.g., a ten-print, a thumb print, etc.) from an arrestee or detainee at time of booking or detention. The print can then be searched against a local or remote database such as the Next Generation Information (NGI) system used by the FBI. The remote fingerprint database can also contain information indicating whether the person has had a DNA sample taken.

According to further specific embodiments, if the system's ten-print capture interface is used to capture the fingerprints, on confirmation from an on-system database, rather than again querying the remote database, the system can match the confirmation fingerprint with the ten-print that it had acquired, saving time to begin processing the DNA sample, and saving capacity for the remote database.

According to further specific embodiments, the user interface portion of system is touchless, indicating that the system receives commands and instructions via audio input or camera input to log on or to authenticate a user via face recognition. For example, the system can "wake up" and/or log a user on or authenticate a user when a voice command is detected or an authorized user positions himself such that the system can capture a facial image.

In further embodiments, a system communicates with a database, such as a criminal records data base, and automatically responds back to a user of the system if there is a match with, for example, a person wanted by a law enforcement agency.

In other embodiments, the system includes operative elements located in predetermined positions that are known to the system. These elements can include, for example, a camera, microphone, fingerprint reader, sample cartridge slot, etc. The user interface can display graphically the positions of specific elements when instructing a user to take actions.

U.S. patent application No. 20130115607 (Priority date Oct. 21, 2011, also published as WO2013059750A1) describes an integrated and automated sample-to-answer system that, starting from a sample comprising biological material, generates a genetic profile in less than two hours, for example where the biological material is DNA and the genetic profile involves determining alleles at one or a plurality of loci (e.g., genetic loci) of a subject, for example, an STR (short tandem repeat) profile, for example as used in the CODIS system. The system can perform several operations, including (a) extraction and isolation of nucleic acid; (b) amplification of nucleotide sequences at selected loci (e.g., genetic loci); and (c) detection and analysis of amplification product. These operations can be carried out in a system that comprises several integrated modules, including an analyte preparation module; a detection and analysis module and a control module.

Various embodiments of the present invention provide methods and/or systems for biometric data interaction over a communications network. According to specific embodiments of the invention, a client system is provided with a set of interfaces that allow a user to view, collect, validate, etc. biometric data. The client system presents information regarding the data and presents indications or instructions regarding actions to a user and displays an indication of an action that a user is to perform to complete the next step of the workflow. In response to a user action and completion of appropriate workflow steps, the client system sends to a server system the necessary information to access or process or verify biometric data. The server system uses the request data, and optionally one or more sets of server data, to process the request. According to specific embodiments of the present invention, a client system is, or has previously been, provided with an executable code file that allows the client system to operate as described herein.

Thus, in further embodiments, the present invention may be understood in the context of facilitation biometric data collection and verification with communication to external data storage or analysis systems over a communication media. An important application for the present invention, and an independent embodiment, is in the field of exchanging biometric data over the Internet or private networks, optionally using Internet media protocols and formats, such as HTTP, RTTP, XML, HTML, dHTML, VRML, as well as image, audio, or video formats etc. However, using the teachings provided herein, it will be understood by those of skill in the art that the methods and apparatus of the present invention could be advantageously used in other related situations where users access content over a communication channel, such as modem access systems, institution network systems, wireless systems, etc.

All publications, patents, and patent applications mentioned in this specification are herein incorporated by reference to the same extent as if each individual publication, patent, or patent application was specifically and individually indicated to be incorporated by reference.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Further in light of the above, specific embodiments can involve systems, methods, or components containing any combination of elements described below. Specific embodiments involve a system comprising an authentication sub-system with a camera and/or a microphone, and a biochemical analysis sub-system configured to perform a biochemical analysis on a biological sample provided to the biochemical analysis sub-system; with the system configured to: (a) authenticate a user by facial recognition based on one or more images taken by the camera or by voice recognition based on voice sound picked up by the microphone, wherein authentication proceeds without an active command from the user; (b) instruct an authenticated user to provide a biological sample to the biochemical analysis sub-system; (c) without further user input, automatically execute a biochemical analysis on a provided biological sample.

Further embodiments involve automatic execution of the biochemical analysis based on instructions stored in system memory, instructions stored on readable memory in the cartridge, or a combination of both. Specific embodiments involve the biological sample provided by insertion of a sample cartridge into a receptacle of a biochemical analysis sub-system. In other embodiments, the authentication system comprises a processor and memory, wherein the memory includes (i) a database of authorized users with authenticating information and (ii) instructions executable by the processor to authenticate authorized users based on images taken by the camera.

In further embodiments, a camera of the system periodically or continually scans the environment for a user that can be authenticated. In other embodiments, the biochemical analysis comprises performing a biochemical reaction on an analyte in the biological sample to produce a reaction product and perform a detection or measurement on the reaction product. In other embodiments, the system is further configured to transmit a result of the biochemical analysis to a remote server and/or to display the result to the authenticated user.

Further embodiments involve one or more digital biometric data capture devices; wherein the system is further configured to instruct the authenticated user to electronically capture biometric data from a subject using at least one of the digital biometric data capture devices. In further embodiments, the digital biometric capture device comprises a camera, a fingerprint reader or a retinal scanner.

Methods according to specific embodiments comprise without an active command from a user, using an authentication sub-system of a system to collect one or more camera images of a user and authenticating the based on the images; instructing an authenticated user through a user interface on the system to provide a biological sample to a biochemical analysis sub-system of the system; and without further user input, automatically executing a biochemical analysis on a provided biological sample.

In further embodiments, biochemical analysis comprises detecting or measuring an analyte in the biological sample directly or indirectly (e.g., by performing a biochemical reaction on the analyte to produce a product, and detecting or measuring the product).

Other embodiments involve a method of collecting biometric data from one or more subjects comprising configuring a biometric capture and biochemical analysis system having at least one logic processor, data storage, at least one biological sample receiver, at least one electronic biometric data capture interface, at least one biochemical analyzer, at least one communications interface, and at least one user presentation interface to perform steps comprising using the user presentation interface to direct a user to prepare a biologic sample and/or to place a biologic sample into a receptacle of the biometric biochemical analysis system; using the user presentation interface to direct said user or a different user to collect electronically captured biometric data from a subject using one or more digital biometric data capture devices; performing a biochemical analysis of the sample using the biochemical analyzer to produce a set of biochemical biometric data; and storing results indicating biochemical biometric data or electronically captured biometric data or both in system memory and/or communicating the results to one or more additional computer systems over the communications interface. Further embodiments involve one or more of executing instructions on the logic processor to authenticate a user; using the user presentation interface to direct a user to collect a biologic sample from one or more subjects. Samples can be one or more selected from saliva, blood, semen, hair, tissues, bodily fluids, a non-living substance suspected of being contaminated with DNA, a swab or other instrument used to sample substances suspected of containing DNA. In further embodiments, the one or more subjects can be one or more selected of: a person being detained, a newborn; a living or deceased victim of an accident or natural disaster, a living or deceased casualty of a military action; a living or deceased victim of a crime or other act of violence; a living or deceased unidentified person; any person; domesticated animals such as livestock, racing animals, pets; wild animals such as research subjects or fisheries catch.

In other embodiments one or more capture devices can be one or more of a still camera; a video camera; an infrared camera or other heat detecting or imaging devices; a scanner for scanning finger prints, hand prints, or foot prints; a retina scanner; a facial scanner; and a microphone for recording audio data. In further embodiments, one of the one or more capture devices are integrated into the biometric biochemical analysis system so as to have a fixed positional relationship to other components of the biometric biochemical analysis system. In specific embodiments at least one of the one or more capture devices are connected to the biometric biochemical analysis system through a local wired or wireless connection so as to allow some independent movement or positioning of the capture device with respect to other components of the biometric biochemical analysis system.

According to further specific embodiments, prior to collecting a biologic sample or one or more items of digitally captured biometric data, querying a database to determine if a subject is known to the database and using whether a subject is known and information about biometric or biological data already on record for the subject to adjust user prompts to direct a user to only capture biometric data or collect a sample when needed or authorized. Specific embodiments allowing one or more users to collect data in an overlapping fashion such that while the biometric biochemical analysis system is performing an analysis or waiting for data from another source, a first user, or an additional user, can receive instructions for collecting digitally captured biometric data or can receive instructions for collecting one or more additional biologic samples for further subjects.

According to specific embodiments, the user presentation interface comprises a display on the biometric biochemical analysis system and directing the user to prepare and/or place a biologic sample comprises displaying textual or graphical instructions on the display directing specific sample preparation and collection actions and deposit of the sample into a receiver. In other embodiments, directing the user to prepare and/or place a biologic sample comprises one or more positional indications alerting a user as to where to place a sample or take some other action with respect to the biometric biochemical analysis system during particular steps of the collection. In further embodiments directing the user to prepare and/or place a biologic sample further comprises presenting one or more step by step instructions to a user, wherein the step by step instructions include at least one instruction specifically indicating a location of a receiver for a sample. In other embodiments, said one or more actions to prepare and/or place a biologic sample comprises: taking a biologic sample from a subject, interacting with the biometric biochemical analysis system to associate the biologic sample with a subject identifier stored by the biometric biochemical analysis system, placing the biologic sample into the sample receiver module.

In other embodiments, the user presentation interface comprises an audio output interface and said directing the user to collect a biologic sample comprises presenting audio prompts to a user either from a speaker on the biometric biochemical analysis system or through an interface directed to a speaker or directed to headphones worn by a user.

In other embodiments, directing the user to prepare and place a biologic sample comprises one or more positional indications alerting a user as to where to position a sample with respect to the biometric biochemical analysis system during particular steps of the collection.

Other specific embodiments are configured for detecting a need for replacement or refilling of one or more components of the system and directing a user via the user presentation interface to perform steps to accomplish the replacement or refilling or detecting a need for a recalibration or revalidation of one or more components of the system and directing a user via the user presentation interface to perform steps to accomplish the recalibration or revalidation or both.

In other embodiments, the system is configured for directing and automating the capture of one or more sets of biometric associated data such as name, address, identification number, incident report, location or condition of subject when found or identified by providing user instructions and indicating capture modules or interfaces using one or more of: audio recording; voice to text recognition; document photographing or scanning; OCR, etc.; and for generating data or instructions for preparing one or more identification labels (e.g., printed labels, printed labels with bar codes; RFID or electronic labels) to attach to a subject; a subjects possessions; other associated objects or substances; or evidence; thereby providing in one system a complete automated process for handling biometric data and associated data of subjects and identifying and labeling further objects; evidence; or possessions associated with subjects.

According to specific embodiments, a system or method as discussed herein involves a system that is substantially portable or transportable and can be moved in a passenger vehicle for biometric data collection and processing in various theaters of operation.

According to further specific embodiments, a system comprises at least one logic processor; data storage; at least one biological sample receiver; at least one electronic biometric data capture module; at least one biochemical analyzer module; at least one communications module; and at least one user presentation module. The processor is configurable with logic instructions to enable the system to perform methods as described herein. In specific embodiments, a method comprises using the user presentation module to direct said user or a different user to collect electronically captured biometric data from a subject using the digital biometric data module; using the user presentation module to direct a user to place a biologic sample into a biological sample receiver and/or to prepare a biologic sample; performing a biochemical analysis of the sample to produce a set of biochemical biometric data; and communicating results indicating biochemical biometric data or electronically captured biometric data or both to one or more additional computer systems over the communications interface. In specific embodiments the at least one biological sample can be one or more of: a cartridge receiver; a cartridge receiver and a cartridge; a liquid sample receiver; a solid sample receiver. In specific embodiments, the least one electronic biometric data capture module can be one or more scanners or cameras for capturing images or scanning data from one or more of: a face or any other part of a body or clothing useful in identification including one or more of prints of fingers, palms, feet, toes, a sample or a sample with a bar code, RFID code, or other code, and an identification card or birth certificate or death certificate or other papers, a retinal scan. According to specific embodiments, one or more audio recorders for capturing a voice print or other audio data and/or one or more interfaces for attaching to external data capture devices can be included.

In further embodiments, electronic biometric data capture modules can be one or more of a still camera, a video camera, an infrared camera or other heat detecting or imaging devices, a scanner for scanning finger prints, hand prints, or foot prints, a retina scanner, a facial scanner, a microphone for recording audio data. or one or more interfaces to connecting to any external capture device. According to specific embodiments, an analyzer can be one or more of: an electrophoresis analyzer; one or more other analyzers or detectors; one or more sample cartridge interfaces; one or more interfaces for attaching to external analyzers or detectors.

In specific embodiments, the logic processor is configured to execute instructions to perform a biochemical reaction on a sample in a sample cartridge engaged with the cartridge interface to produce a reaction product and to analyze the reaction product.

In other embodiments, at least one additional analyzers or detectors are included and can be one or more of one or more medical examination detectors able to determine one or more of heart rate, temperature, blood pressure, or other medical parameters; one or more detectors for detecting drugs or alcohol or other parameters from body sample such as hair, blood, skin, or urine; one or more detectors for detecting drugs or alcohol or other parameters from a breath sample.

A communication interface according to specific embodiments can be one or more of a wired or wireless connection to a local area network; a wired or wireless connection to an external connection, such as the internet; and a wired or wireless connection to one or more local devices or systems. A user presentation interface according to specific embodiments can be one or more of multipurpose displays for presenting video, image, or text content, audio devices, more visual or audio indicators for indicating a state of a particular part of component of the system, interfaces for external presentation devices. In further embodiments, system components are operationally connected into effectively one system with a user presentation interface configured to direct collection of both a sample and to capture biometric data and/or configured into a physical housing that provides a substantially unified physical system.

In various embodiments, the processor is configurable to use one or more of the modules to authenticate a user and/or to use one or more of said modules to direct a user to collect a biologic sample from one or more subjects.

Various embodiments involve samples that are one or more of saliva, blood, semen, hair, tissues, bodily fluids, a non-living substance suspected of being contaminated with DNA, a swab or other instrument used to sample substances suspected of containing DNA and/or subjects that are one or more selected of a person being detained, a newborn; a living or deceased victim of an accident or natural disaster, a living or deceased casualty of a military action; a living or deceased victim of a crime or other act of violence; a living or deceased unidentified person; any person; domesticated animals such as livestock, racing animals, pets; wild animals such as research subjects or fisheries catch.

In further embodiments the at least one electronic biometric data capture module comprises one or more capture devices integrated into the biometric biochemical analysis system so as to have a fixed positional relationship to other components of the biometric biochemical analysis system and/or one or more capture devices connected to the biometric biochemical analysis system through a local wired or wireless connection so as to allow some independent movement or positioning of the capture device with respect to other components of the biometric biochemical analysis system.

In further embodiments, the processor is further configurable to prior to collecting a biologic sample or one or more items of digitally captured biometric data, query a database to determine if a subject is known to the database and using whether a subject is known and information about biometric or biological data already on record for the subject to adjust user prompts to direct a user to only capture biometric data or collect a sample when needed or authorized and/or to allow one or more users to collect data in an overlapping fashion such that while the biometric biochemical analysis system is performing an analysis or waiting for data from another source, a first user, or an additional user, can receive instructions for collecting digitally captured biometric data or can receive instructions for collecting one or more additional biologic samples for further subjects.

According to specific embodiments, the processor is further configurable to use the user interface to direct the user to prepare and place a biologic sample comprises displaying textual or graphical instructions on the display directing specific sample preparation and collection actions and deposit of the sample into a receiver and in specific embodiments, directing the user to prepare and place a biologic sample comprises one or more positional indications alerting a user as to where to place a sample or take some other action with respect to the biometric biochemical analysis system during particular steps of the collection and/or directing the user to prepare and/or place a biologic sample by presenting one or more step by step instructions to a user, wherein the step by step instructions include at least one instruction specifically indicating a location of a receiver for a sample. In specific embodiments, one or more actions to prepare and place a biologic sample involve taking a biologic sample from a subject, interacting with the biometric biochemical analysis system to associate the biologic sample with a subject identifier stored by the biometric biochemical analysis system, placing the biologic sample into the sample receiver module. In other embodiments, an audio output interface can direct the user to collect a biologic sample comprises presenting audio prompts to a user either from a speaker on the biometric biochemical analysis system or through an interface directed to a speaker or directed to headphones worn by a user. In other embodiments, directing the user involves one or more positional indications alerting a user as to where to position a sample with respect to the biometric biochemical analysis system during particular steps of the collection.

Further embodiments involve a method incorporating any combination of the elements described above or a system configured to carry out a method incorporating any combination of the elements described above. Other embodiments involve a nontransitory computer readable medium containing computer interpretable instructions that when loaded into an appropriately configured information processing device will cause the device to operate in accordance with a method incorporating any combination of the elements described above.

Other embodiments involve a method or a system for collection and analysis of biometric data from subjects by non-technical users at an integrated biometric data collection and analysis system, the system comprising a logic processor operationally connected to: a memory, a user interface, a biometric data collection component, a biological sample receiver, a biochemical analysis component, and a communications component, the method comprising: configuring the at least one logic processor of the system to execute a logic routine able to: authenticate a user using the user interface; direct the user using the user interface to input initial data regarding a subject using the user interface or the biometric data capture component or both; perform an initial search using the initial data and indicate to a user progress of the initial search using the user interface; determine if a biometric sample should be collected and, if yes, direct the user using the user interface how to do any of: collect the biologic sample, identify the sample to the system, or place the sample into the biological sample receiver for biologic analysis; on completion of a biologic analysis, transfer biologic analysis data results for forensic identification; optionally, indicate to a user progress of the biologic analysis and progress of the transfer using the user interface; optionally, indicate to a user when to remove the sample from the system and further handling of the sample; receive data regarding forensic identification; and present data regarding forensic identification to the user using the user interface.

BRIEF DESCRIPTION OF THE DRAWINGS

The novel features according to specific embodiments are set forth with particularity in the appended claims. A better understanding of the features and advantages will be obtained by reference to the following detailed description that sets forth illustrative embodiments and the accompanying drawings (also "figure" and "FIG." herein), of which:

FIGS. 1A-1C are flow charts illustrating methods of collecting biometric data according to specific embodiments of the invention.

DESCRIPTION OF SPECIFIC EMBODIMENTS

Figure 1B:
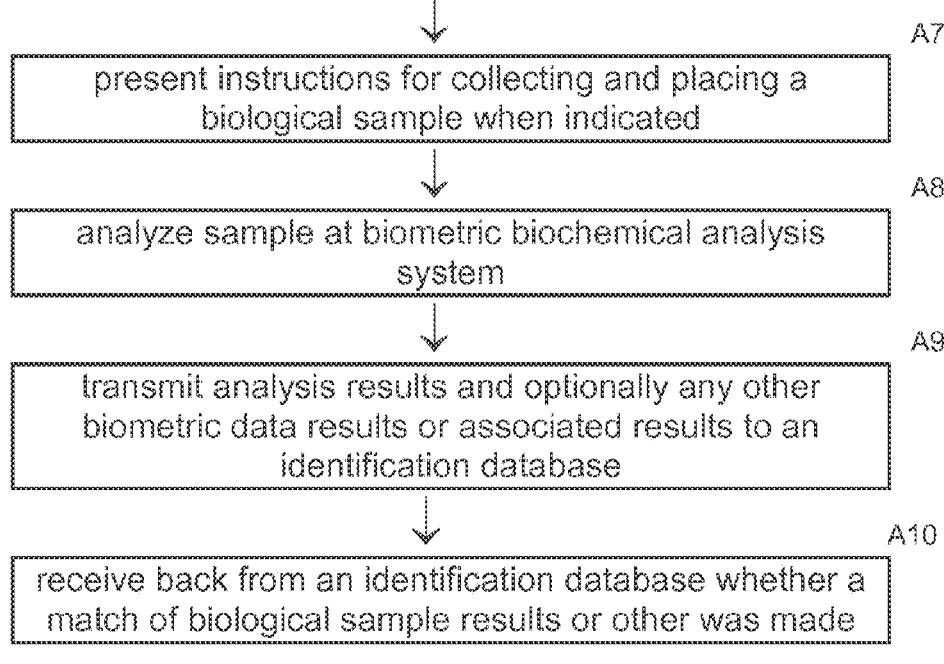
Figure 2:
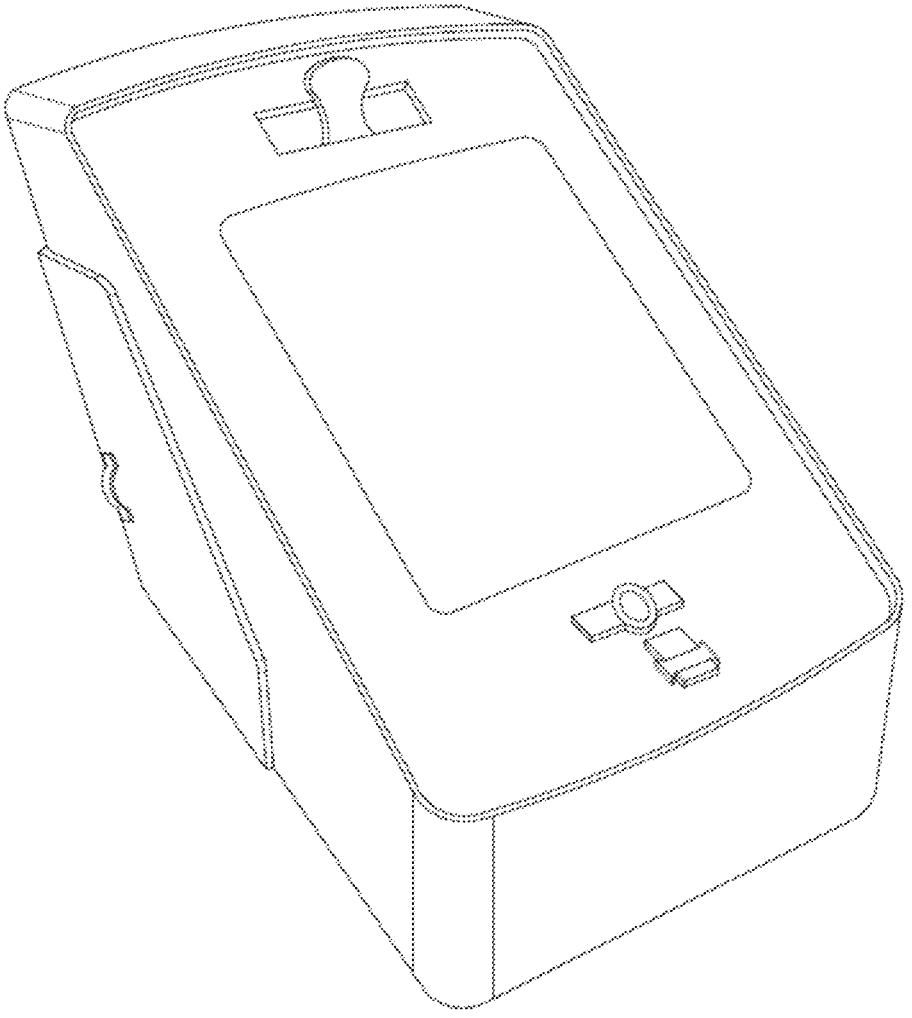
FIG. 2 is a photograph showing example external features and appearance of a biometric biochemical analysis system according to specific embodiments.

Before describing the present invention in detail, it is to be understood that this invention is not limited to particular compositions or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content and context clearly dictates otherwise. Thus, for example, reference to "a device" includes a combination of two or more such devices, and the like.

Unless defined otherwise, technical and scientific terms used herein have meanings as commonly understood by one of ordinary skill in the art to which the invention pertains. Although any methods and materials similar or equivalent to those described herein can be used in practice or for testing of the present invention, the preferred materials and methods are described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

The term "sample", as used herein, refers to a sample containing biological material. A sample may be, e.g., a fluid sample (e.g., a blood sample) or a tissue sample (e.g., a cheek swab). A sample may be a portion of a larger sample. A sample can be a biological sample having a nucleic acid, such as deoxyribonucleic acid (DNA) or ribonucleic acid (RNA), or a protein. A sample can be a forensic sample or an environmental sample. A sample can be pre-processed before it is introduced to the system; the preprocessing can include extraction from a material that would not fit into the system, quantification of the amount of cells, DNA or other biopolymers or molecules, concentration of a sample, separation of cell types such as sperm from epithelial cells, concentration of DNA using an Aurora system (Boreal Genomics) or bead processing or other concentration methods or other manipulations of the sample. A sample can be carried in a carrier, such as a swab, a wipe, a sponge, a scraper, a piece punched out a material, a material on which a target analyte is splattered, a food sample, a liquid in which an analyte is dissolved, such as water, soda. A sample can be a direct biological sample such as a liquid such as blood, semen, saliva; or a solid such a solid tissue sample, flesh or bone.

Systems discussed herein can also be applied to process and analyze a sample that has been previously preprocessed, for example, by extraction of DNA from large object such as a bed sheet or chair and other processing which may include quantification of DNA concentration, cell concentration, or other manipulations before input of the pre-processed sample into the sample cartridge of the system. DNA can be analyzed by amplification (e.g., PCR) followed by capillary electrophoresis or by DNA sequencing, e.g., high throughput sequencing.

"Biometric data" as used herein generally refers to any data used to identify an individual, group of individuals, or any biologic entity or group that is a measurement or image of a biologic system. For purposes of this discussion, biometric data comprises without limitation, fingerprints, hand and foot prints, facial or body recognition, DNA or protein recognition, blood or tissue recognition, voice prints or vocal recognition, dynamic or static signature information, gait recognition, height, weight, dental records or x-rays, etc. "Biometric data" can also encompass other identifying information, such as date of birth, government issued ID number, etc.

"Digitally captured biometric data" as used herein generally refers to any data used to identify an individual, group of individuals, or any biologic entity or group that is a measurement or image of a biologic system that is generally directly captured from a subject as digital data without requiring substantially further analysis or processing. For purposes of this discussion, biometric data comprises without limitation, fingerprints, hand and foot prints, facial or body recognition, voice prints or vocal recognition, dynamic or static signature information, gait recognition, height, weight, dental records or x-rays, etc. "Biometric data" in some contexts can also encompass other identifying information, such as date of birth, government issued ID number, etc.

"Biochemical biometric data" as used herein generally refers to any data used to identify an individual or any biologic entity or group that is that is based on detecting one or more chemical or biological properties. For purposes of this discussion, "biochemical biometric data" biometric data comprises without limitation, DNA or protein recognition, blood or tissue recognition, or other chemical or biological substance analysis. For example, biochemical biometric data can include short tandem repeat (STR) profiles, genetic ancestry profiles and genomic sequence data.

Overview

According to specific embodiments, data processing or information or computer systems and/or methods and/or operational methods that can be used together to as described herein. Systems and methods as described herein in various embodiments and some of the benefits and features of these embodiments can be understood as including any combining of the following: (1) integration and automation of previously disparate workflows; (2) higher confidence of chain of custody of biometric data; (3) portability; (4) ease of use; (5) decreased costs; (6) increased speed; (7) increased efficiency; and (8) configurable operation to allow optimizing workflow in different operating environments (booking room, hospital, disaster site, morgue, etc.) and in different legal or procedural regimes (e.g., legal restrictions on when and whether DNA samples may be taken, legal requirements for video documenting one or more steps of biometric data or sample gathering, institutional or legal requirements for preserving, linking, or verifying specific types of biometric data and associated data generated during a data collection process, etc.)

In one embodiment, the present invention provides a method and/or system for biometric data collection and verification in a client/server environment.

Systems

Recognized herein is the need for highly integrated and automated systems and methods for collecting digitally captured and biochemical biometric data, including instructing users on digital capture, sample collection, sample preparation, and on automatically processing and analysis. Systems provided herein may be capable of preparing, processing and analyzing a single sample or a plurality of samples. Several automated sample handling operations can be performed by the system provided herein, for example, (a) receiving one or more samples; (b) isolating and extracting target material from the received sample; (c) purifying and amplifying the whole target material or selective portion of the target material to produce an analyte ready to be examined; and (d) separating, detecting and analyzing the prepared analyte. These operations can be conducted and performed in a system that comprises several integrated sub-systems, for example, at least about 1, 2, 3, 4, 5, 6, 7, 8, 9, 10, 20, 30, 40, or 50 sub-systems. In some cases, a system may comprise a user interface, a sample cartridge interface, and an electrophoresis interface. The sample cartridge interface and the electrophoresis interface are configured to releasably engage with a sample cartridge for sample processing, and an electrophoresis cartridge for sample analysis respectively. Systems provided herein can be fully automated, enabling a user to receive, process and analyze a sample without substantial labor and input. Sample preparation, processing and analysis can be accomplished in provided systems without the necessity of manually removing and transferring the sample, reagents and analytes among different parts in the system. Since the incorporated sub-units (e.g., sample cartridge and electrophoresis cartridge) are highly integrated and bear small sizes, systems provided herein can be dimensioned to minimize footprint, enabling the portability and usefulness in a wide context of applications. For example, the systems may be used in on-the-go situations, such as remote locations. Or they may be used in situations in which transportation is not readily available or user mobility is desired, such as battlefields scenarios.

Figure 3A:
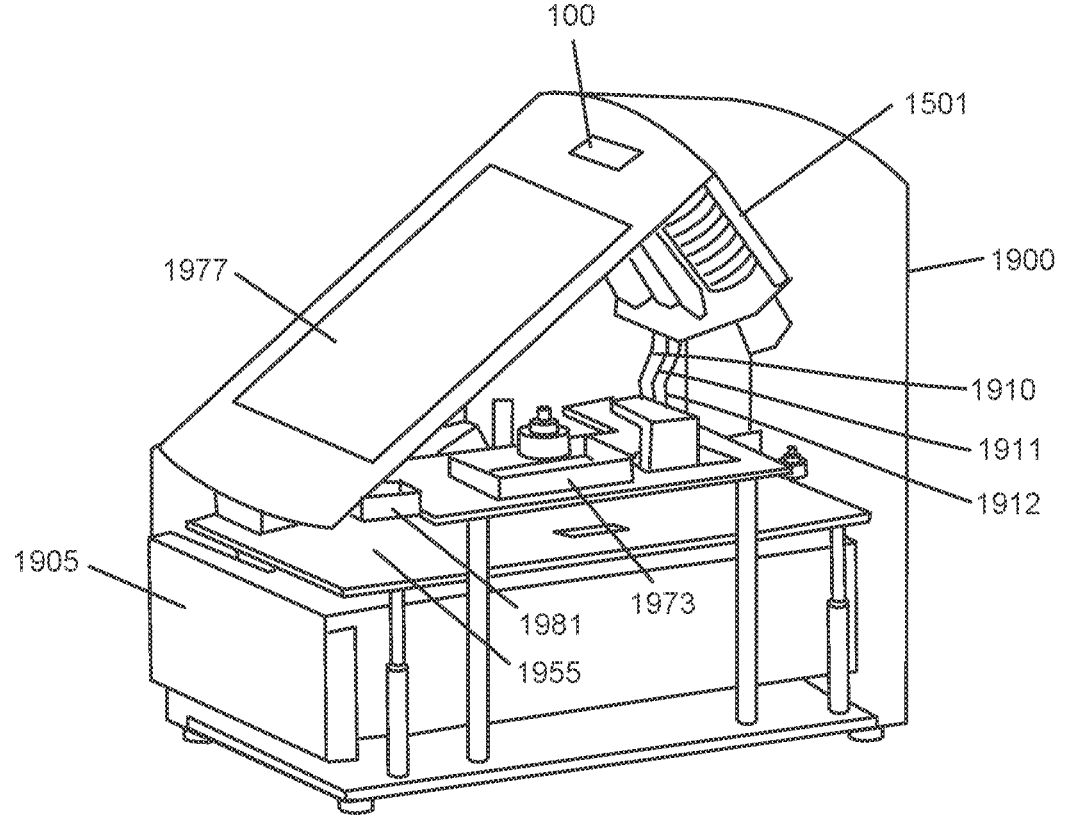
FIGS. 3A-3D illustrate features and aspects of example biometric biochemical analysis systems according to specific embodiments.
Figure 3B:
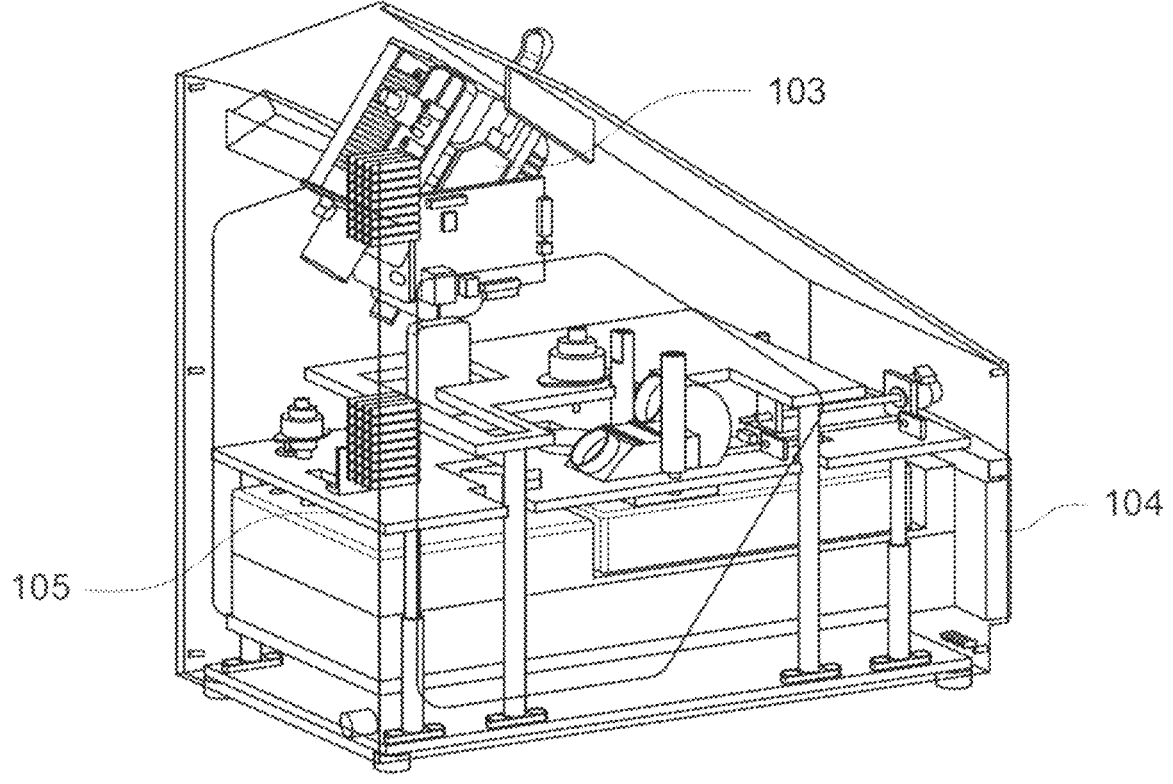
Figure 3C:
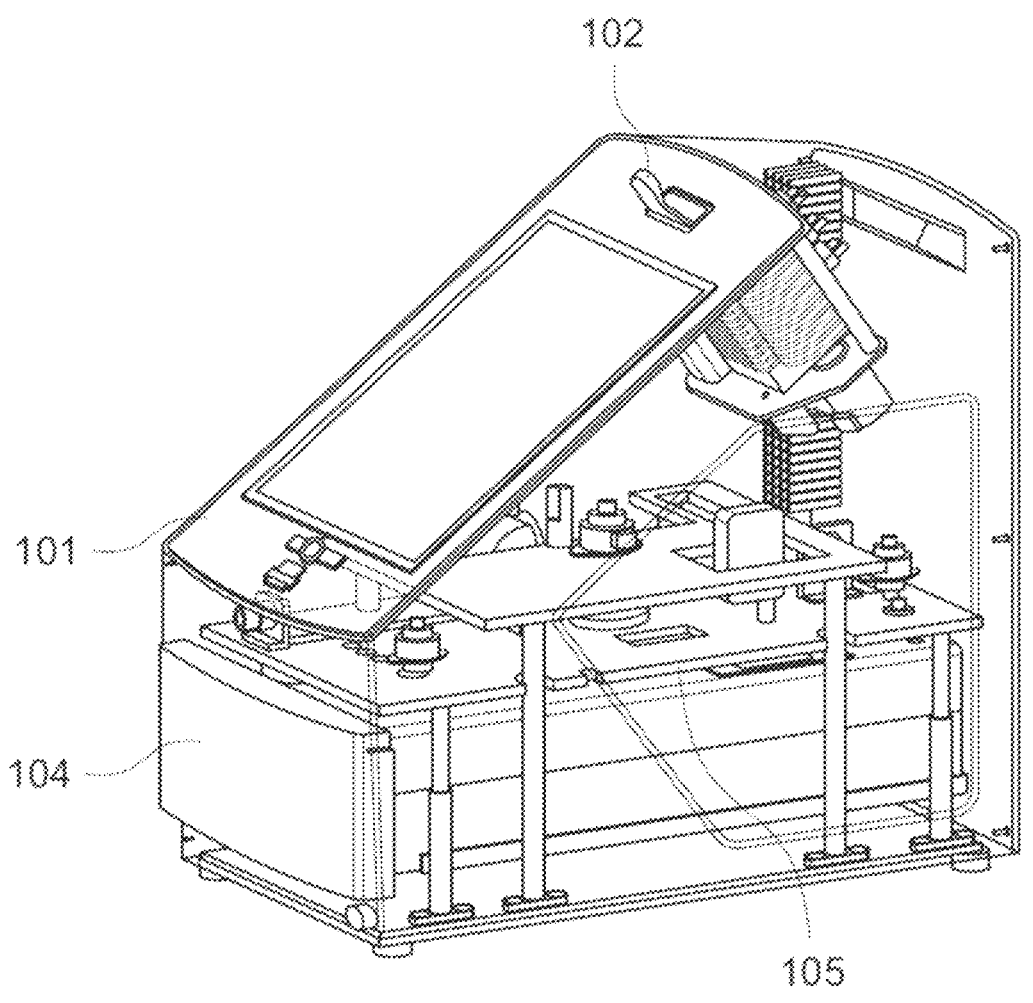

FIG. 3A-C illustrate features and aspects of example biometric biochemical analysis systems according to specific embodiments FIG. 3A illustrates a system for sample processing and analysis. System 1900 can include several functional elements. System 1900 can include a sample preparation sub-system, a sample analysis sub-system and a control sub-system. A sample preparation sub-system of the system 1900 can include a sample cartridge interface 1501 configured to engage a sample cartridge 102, sources of reagents for performing a biochemical protocol, a fluidics assembly configured to move reagents within the sample preparation sub-system. A fluidics assembly can include a pump, such as a syringe pump. The pump is fluidically connectable through valves to the outlets for reagents such as water and lysis buffer and to a source of air. The pump can be configured to deliver lysis buffer and water through fluidic lines 1910 and 1911, respectively, to inlet port 1912 in the sample cartridge. Air or liquid pressure applied by the pump to inlet port 1912 can pump analyte out outlet port 1913 and through line 1912 into the analyte inlet in the electrophoresis cartridge.

Electrophoresis is the motion of dispersed particles relative to a fluid under the influence of a spatially uniform electric field. It may be caused by the presence of a charged interface between the particle surface and the surrounding fluid. Electrophoresis is the basis for a number of analytical techniques used in biochemistry for separating molecules by size, charge, or binding affinity.

FIG. 3B and FIG. 3C present the system of FIG. 3A in further detail. As described above, a sample cartridge interface 103 and an electrophoresis interface 105 are comprised in the system, for engaging the sample cartridge and the electrophoresis cartridge. Both the sample cartridge and the electrophoresis cartridge provided herein can be releasably or removably engaged with the system. The system of FIG. 3A-C can be used in forensic analysis to generate genetic information, such as an STR profile, from a single sample. In some cases, the system may be used to determine the genetic profile of a sample in less than about 6 hours, 5 hours, 4 hours, 3 hours, 2.5 hours, 2 hours, 1.5 hours, 1 hour, 30 minutes, 20 minutes, 10 minutes, 5 minutes 1 minute or less. Such time may depend upon the number of steps included in sample processing operations, for example.

Figure 3D:
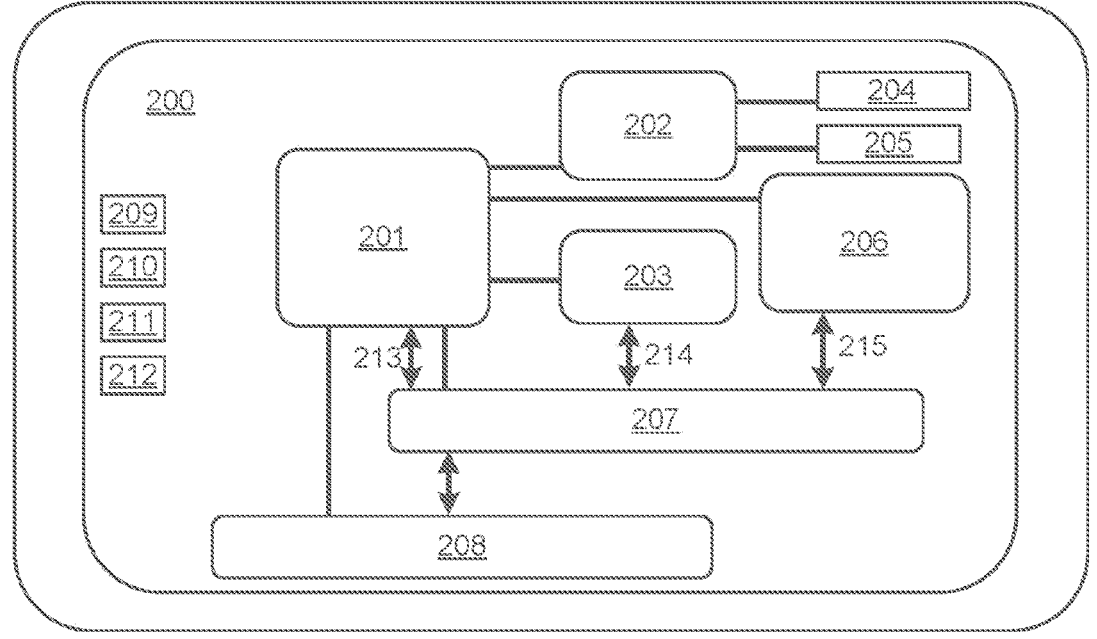

A schematic of the system of FIG. 3A-C is illustrated in FIG. 3D. A chassis 200 is included for structural support, which may be formed of a metallic material, such as aluminum or steel, a polymeric material, or a combination thereof. In some cases, the chassis may be structured to minimize the weight of the system. A user interface which comprises system electronic controls 201, embedded computer 202, and a user interface screen capable of identifying and reading fingerprint 204 and sample patch barcode 205, is included in the system. The user interface receives and processes requests or instructions from and delivers information to a user. It can include software programmed to execute routines for performing the operations mentioned, above, and transmit and receive information, such as computer files, from remote locations, e.g., over the Internet. The user interface can also enable the user to monitor the progress of the operation and make changes to the operation of system if measurements are not within selected parameters. A sample cartridge interface 206 is provided for receiving a sample cartridge for sample processing. The sample cartridge described herein can be configured to receive one or more samples and to perform at least one of sample isolation, extraction, purification, biochemical reaction (e.g., DNA amplification) or dilution, when the sample cartridge is engaged with the sample cartridge interface of the system. Sample amplification can include polymerase chain reaction (PCR). One or more reagents that are needed for performing one or more steps of sample processing may be pre-loaded or comprised in the sample cartridge, for example, washing buffer, lysis buffer, diluent, or amplification reagents. Also comprised in the system is a fully integrated electrophoresis cartridge 207 that is releasably engageable with the system via an electrophoresis cartridge interface. The electrophoresis system comprises all essential parts for performing an electrophoretic analysis, such as an electrophoresis capillary, electrodes (e.g., anode and cathode), electrophoresis separation medium, or electrophoresis buffer. It may further comprise one or more reagent containers for holding reagents that are used for sample processing, e.g., a lysis buffer container. The lysis buffer may be placed in fluidic communication with the sample cartridge and used for isolating the target material out of the sample during sample processing, after both the sample cartridge and the electrophoresis cartridge are engaged with the system. Once the engagement of the electrophoresis cartridge is completed, at least one automatic communication between the electrophoresis cartridge and the system may be established, for example, an electrical communication 213 between the electrophoresis cartridge and the system electronic controls 201, an optical communication 214 between a portion of the electrophoresis capillary in the electrophoresis cartridge and an optics module 203 of the system, a fluidic communication 215 between a sample inlet port of the electrophoresis cartridge and a sample outlet port of the sample cartridge, a mechanical and thermal 216 communication between the electrophoresis cartridge and a motorized drives and cooling module 208 of the system. Accordingly, sample analysis can include isolation of an analyte, such as DNA, from a sample, performance of a chemical reaction on the analyte, such as PCR, to produce a reaction product (e.g., STR amplicons) and analysis of the reaction product, e.g., detection and analysis reaction product by electrophoresis.

The system provided herein may further comprise a power source 212 for supplying the power for the system, AC mains 211 for applying a voltage gradient across the anode and the cathode, one or more fans 210 for dissipate the heat for one or more parts of the system, and one or more USB ports 209 for collecting and transferring data either within the system or outside the system.

User Interface

Figure 4A:
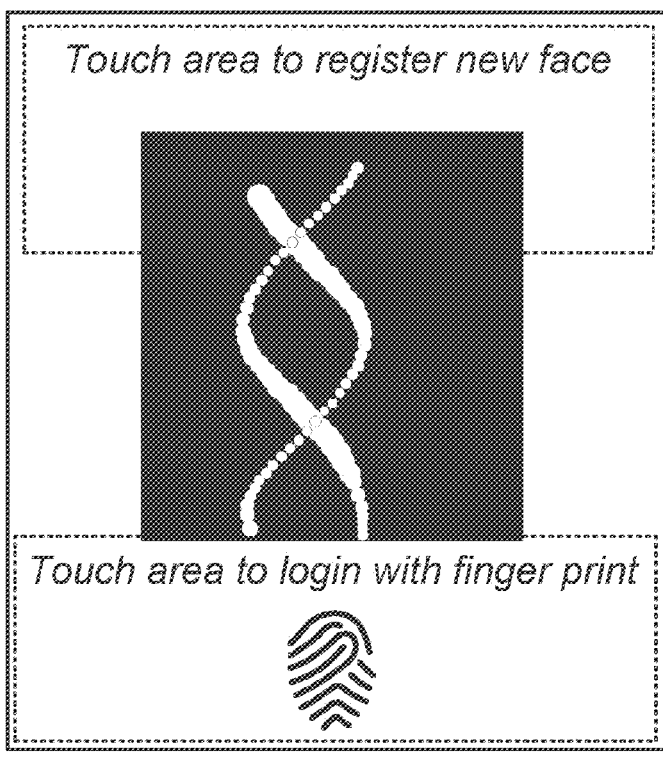
FIGS. 4A-4AB illustrate a series of example graphical user interface screens that are displayed on a biometric biochemical analysis system display according to specific embodiments.

FIGS. 4A-4AB illustrate a series of example graphical user interface screens that are displayed on a biometric biochemical analysis system display according to specific embodiments. These screens are provided as one illustrative example only. It will be apparent to one of skill in the art that many modifications, substitutions, and rearrangements are possible. It was also be apparent to one of skill in the art that any portion of the screen may include video content where desired or helpful, including animated diagrams. It will be further apparent that one or more screens may be accompanied by appropriate audio output.

FIGS. 4A-4AB also illustrate examples of representative directed workflows according to specific embodiments. As further described herein, these workflows represent separate novel aspects when related to a biometric biochemical analysis system as discussed herein.

FIG. 4A, screen 1, illustrates an example optional login, or start, or "lock" interface according to specific embodiments. Note that in this and other screens, text presented in italics is generally descriptive of a screen region and is generally not displayed to a user. In this example screen, a user can login or authenticate herself or himself, either to begin a new session or continue a session in progress, by placing a thumbprint or other print on an area indicated by the GUI. This area may be on the display itself or on some other reading portion of a biometric biochemical analysis system that is indicated by the system. In further embodiments, a biometric biochemical analysis system includes a camera that can perform user face detection that is active as programmed by the system (e.g., at all times when the system is on or at specific times) and that recognizes and authorizes a user as soon as the user is positioned near the system and/or when the user performs a touch or audio request for authentication. The screen further optionally includes a touch area or other input that can be activated to register a new user according to any user registration method.

Figure 4B:
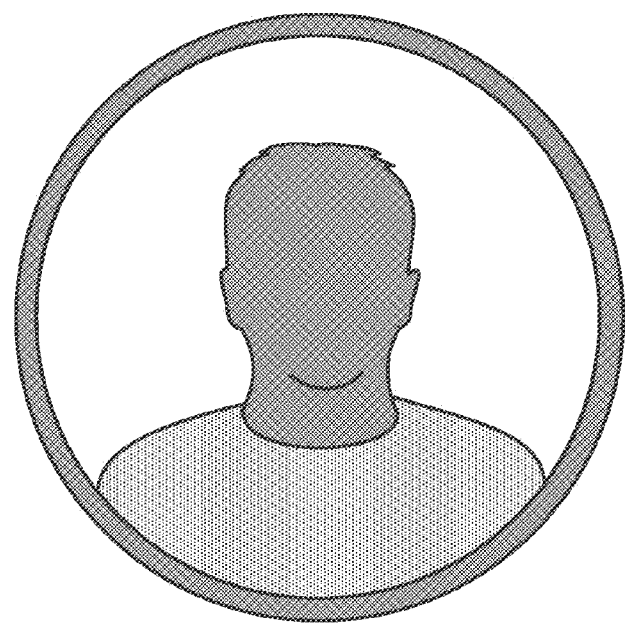

FIG. 4B, screen 2, illustrates an example of user recognition or authentication according to specific embodiments. Generally, a user will be acknowledged as recognized and authenticated by a display of an official stored photograph of the user as shown. Alternately, a user's name or other indicia (e.g., employee identification number) may be displayed or presented audibly. According to specific embodiments, the user's identity will be shown on the display at various times throughout the collection process both to alert the user that he is still the authenticated user and to allow possible other users to determine whether a biometric biochemical analysis system is in use and by whom.

In certain embodiments, user authentication is automatic, that is, a user is authenticated without providing an active command to the system. For example, authentication can occur without providing any of: a physical cue, such as touching a screen or pressing a button; a visual cue, such as providing a visual sign such as a waving motion, or verbal cue, such as announcing, "Hey, System". In such an embodiment, the system can have a camera that continually or periodically scans the environment looking for any faces, and software that analyzes facial images for a potential user. Using, e.g., facial recognition software, the system can match an image with an authorized user, and authenticate the user. Facial recognition software is commercially available, e.g., from Luxand (Alexandria, VA) or iViewSystems (Oakville, Ontario, CA). Alternatively, a microphone can be on continuously or intermittently. Speaker recognition can recognize voices for authentication, and can do so without a prompt from a user to "listen" to a command. Speaker recognition software is commercially available, e.g., from Sestek (Istanbul, Turkey). System operation can continue once a user is authenticated.

Figure 4C:
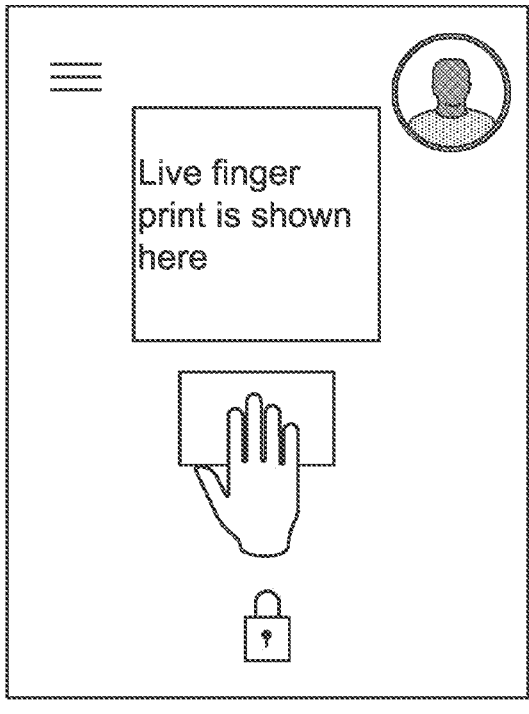

FIG. 4C, screen 3, illustrates an example of a display directing a user to capture biometric data, in this example a set of fingerprints from a subject. The biometric data may be captured by an area of the display, such as a touch screen or reader or cameras integrated with the display. Alternatively, the biometric data may be captured by another module or component of a biometric biochemical analysis system, in which case the location and operation of that module or component will be indicated on the screen. This screen optionally also includes a "lock" icon to return a biometric biochemical analysis system to a "locked" status, thereafter requiring a user to be authenticated again before performing further tasks regarding this particular session or any session. The lock icon can be repeated on various other screens as illustrated or as desired and configured according to specific embodiments. This screen optionally also includes a user identification indication, in this case a photograph shown on the upper right, to indicate to the user or to others which user is actively performing a task on the biometric biochemical analysis system. This identification indication can be repeated on various other screens as illustrated or as desired and configured according to specific embodiments. This screen optionally also includes a menu activation indication, in this case a graphic shown on the upper left, to allow a user to activate one or more menus of the biometric biochemical analysis system as described further herein. This indication can be repeated on various other screens as illustrated or as desired and configured according to specific embodiments. The menus presented can be context sensitive providing different options or a different arrangement of options or submenus depending of the context of the activation. Optionally, the screen can also show an indication of the biometric data being captured and processes being performed, such as a search. In this example, a fingerprint capture is indicated with a live display shown of the captured data. Various information about the capture can also be displayed, such as elapsed or expected time to process or store the capture, quality of the capture, indication that the capture should be repeated, etc.

Figure 4D:
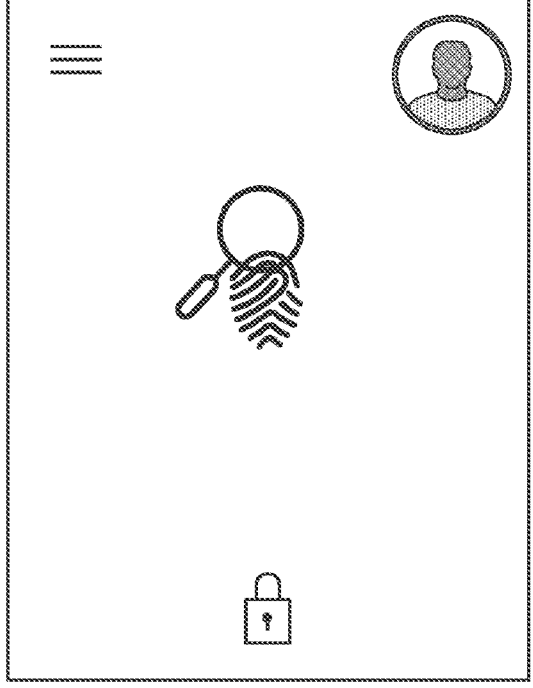

FIG. 4D, screen 4, illustrates an example of a display indicating that the system is awaiting search results from a server, results from a remote database such as Integrated Automated Fingerprint Identification System (IAFIS). In this example, a fingerprint database is indicated. Various information about the search can also be displayed, such as elapsed or expected time, database to be searched, number of records searched, etc.

Figure 4E:
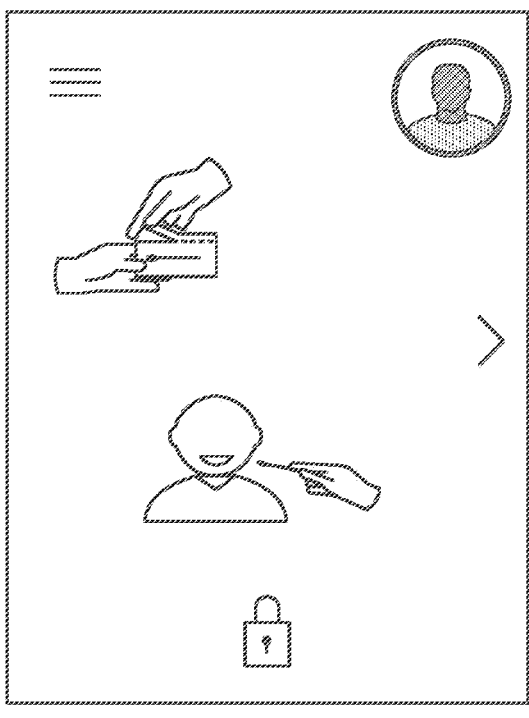
Figure 4F:
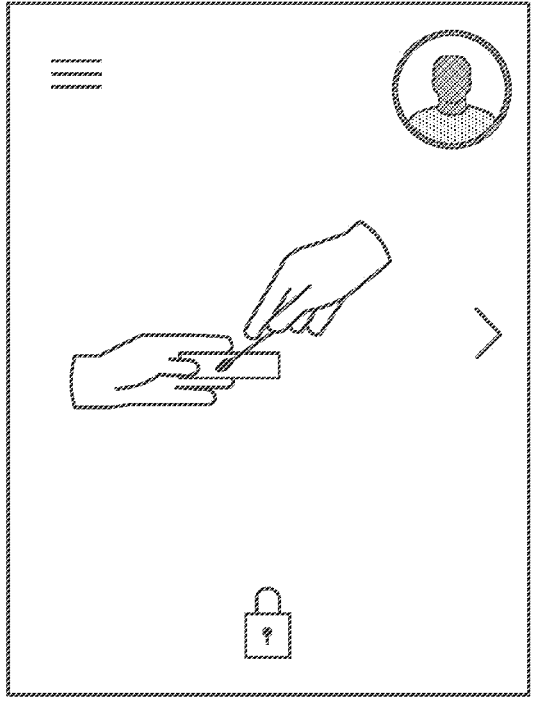

FIGS. 4E-4F, screens 5 and 6, illustrate an example of a display directing a user to perform one or more steps to prepare a biologic sample. As elsewhere described herein, display of this screen may be conditional on results from a fingerprint search or results of some other action of the biometric biochemical analysis system. As elsewhere described herein, a biometric biochemical analysis system for one or more reasons may determine that collection of a particular biologic sample is or is not desirable, needed, or authorized. In this example, directions are illustrated showing a user how to take a saliva sample from a subject using a "swab" or similar device. As will be understood from the discussion herein to one of ordinary skill in the art, display of one or more subsequent screens is conditional on whether this screen is activated for sample collection.

Figure 4G:
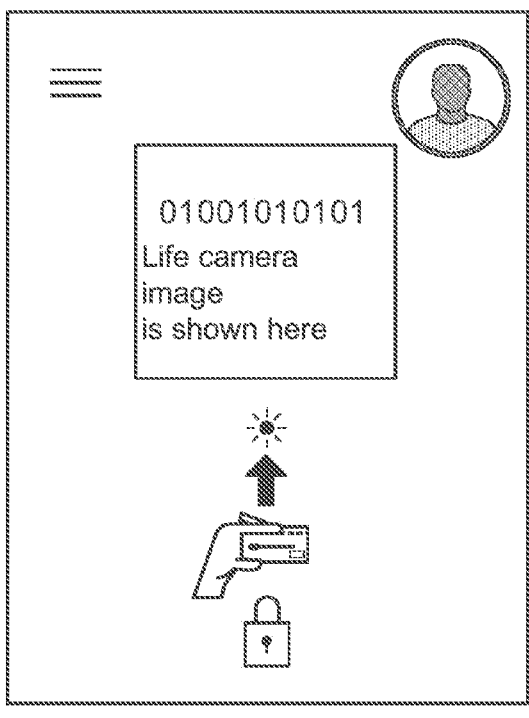

FIG. 4G, screen 7, illustrates an example of a display directing a user to scan a code associated with a sample (e.g., a bar code or QR code associated with a swab or swab container or envelope). In this example, a live camera image of the code is displayed along with the recognized code contents.

Figure 4H:
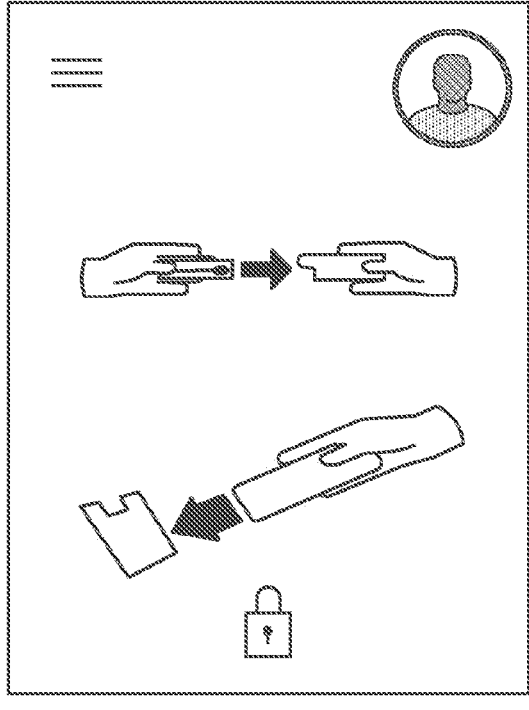

FIG. 4H, screen 8, illustrates an example of a display directing a user to perform one or more steps to place or submit a sample at or in a correct portion of the biometric biochemical analysis system. As elsewhere described herein, display of this screen may be conditional on results from a fingerprint search or results of some other action of the biometric biochemical analysis system. In this example, directions are illustrated showing a user how to take one saliva swab from an envelope or container that has been registered to the system and place that swab into an analysis portion of the biometric biochemical analysis system.

Figures 4I, 4J:
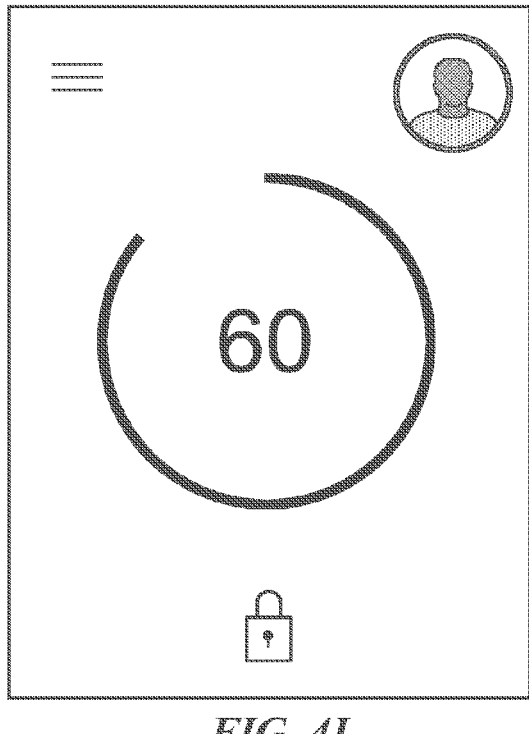
Figure 4K:
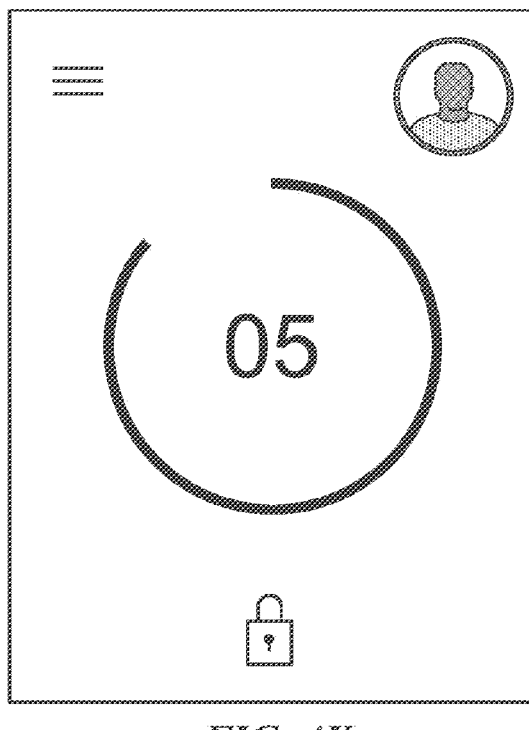

FIGS. 4I, 4J and 4K, screens 9, 10, and 11, illustrate a timer displayed according to specific embodiments. This timer is displayed because biologic analysis can take substantial time, e.g., 60 minutes. The timer alerts the user or other users that the biometric biochemical analysis system is performing a biochemical analysis that generally can only be paused or aborted by the user that initiated the analysis or optionally another user specifically authorized to abort such analysis. As described elsewhere herein, this screen may optionally include an icon or indication, such as the menu indication at the top left, that allows a user to use the biometric biochemical analysis system for further data collection of a current subject or a different subject while the analysis proceeds.

Figure 4L:
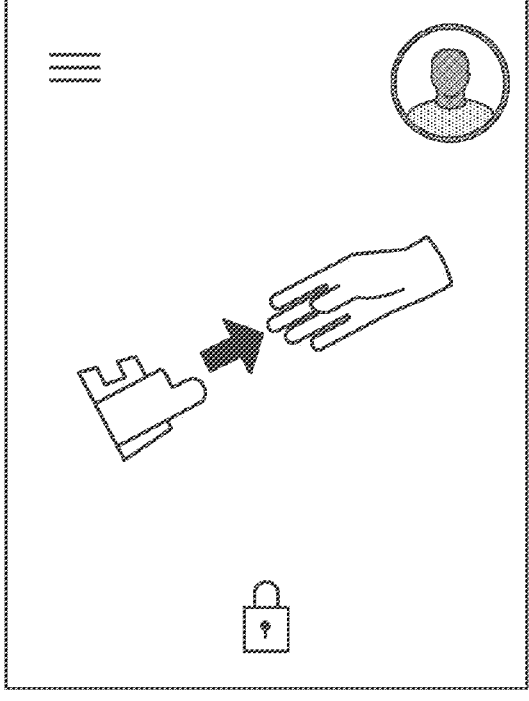

FIG. 4L, screen 12 illustrates an example of screen directing a user to remove a spent or completed component from a system, in this case a sample for which analysis is complete.

Figure 4M:
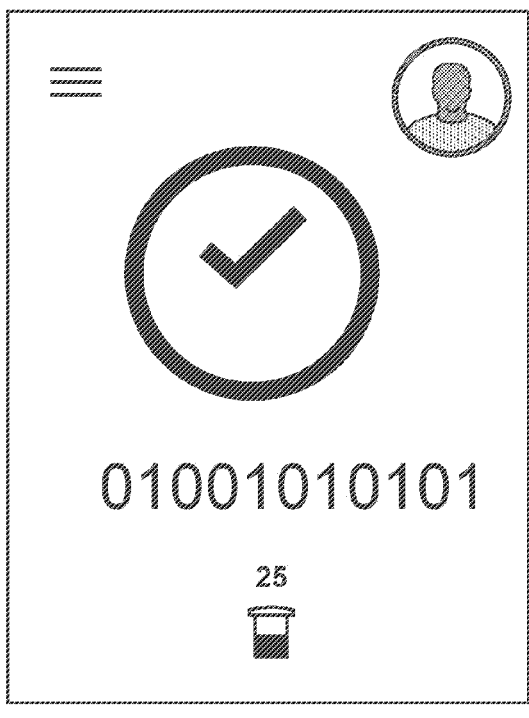

FIG. 4M, screen 13 illustrates one example of a task complete screen. In this example, the completed task is the analysis and the example screen indicates an identification number for the subject and/or the analysis. The screen also indicates a back end cartridge (BEC) icon and a number of analysis (e.g., "25") that can be performed before the BEC must be replaced.

Figure 4N:
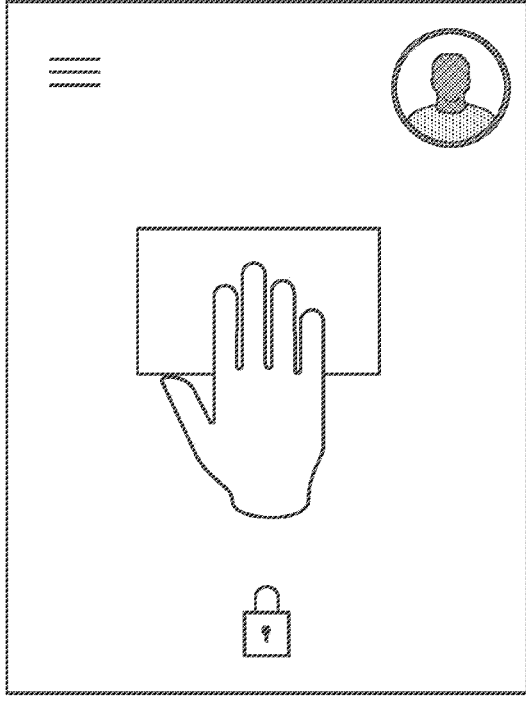

FIG. 4N, screen 14 illustrates one example of directing a user to take a confirmation action or confirmatory data with respect to a biometric data collection task. In this example, a user is directed to again fingerprint a subject with respect to a DNA sample collection to confirm the subject matches the analyzed DNA. Note, this confirmatory action may take place at any time with respect to the workflow as is required by legal or institutional authorities. Other confirmatory tasks may include a video recording of a subject having a sample collected and/or holding a labeled sample once collected, an audio recording of a subject reading out a sample number, etc. These confirmatory tasks can be prompted at the start or end of sample analysis or during collection.

Figure 4O:
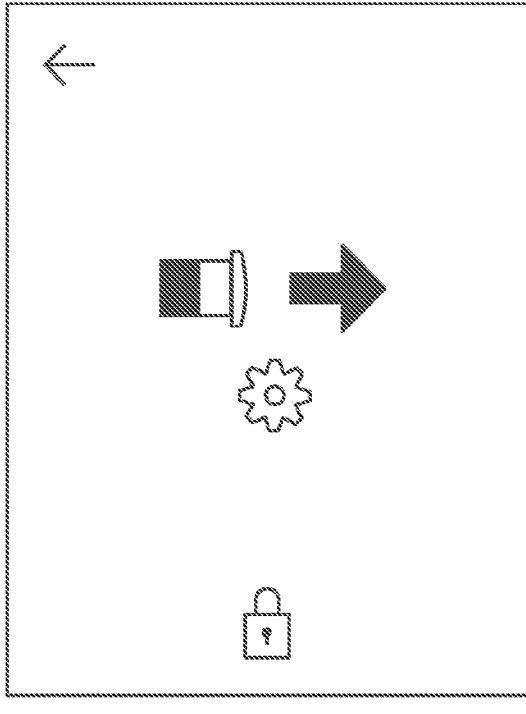
Figure 4P:
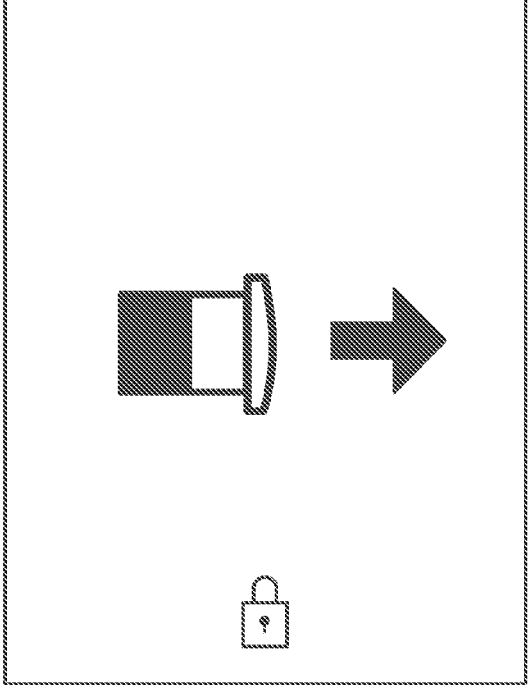
Figure 4Q:
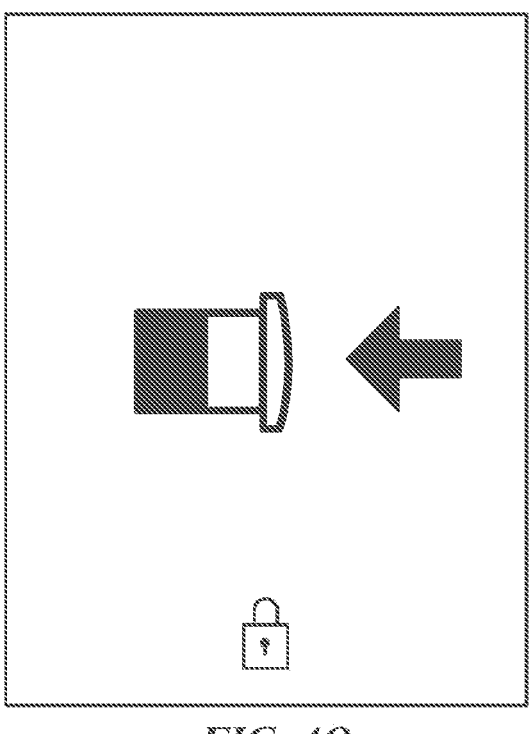
Figure 4R:
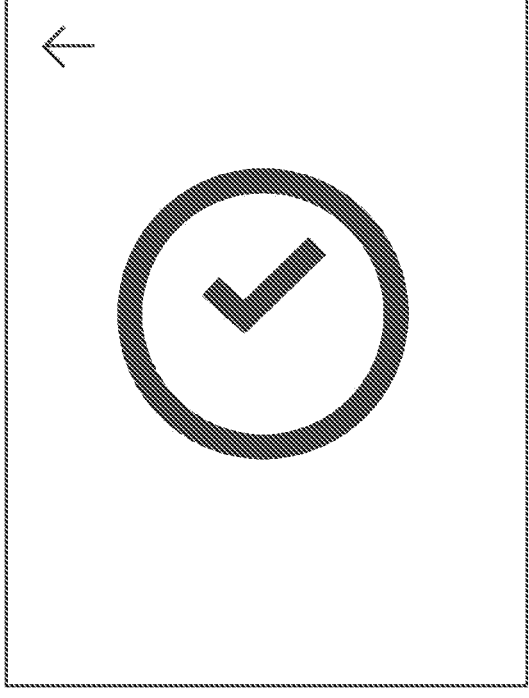

FIGS. 4O, 4P and 4Q, screens 15, 16, and 17, illustrate an example of a display directing a user to perform one or more steps to place one or more reagents, supplies, or other supplemental or support components in a correct location of the biometric biochemical analysis system. Display of this screen is generally triggered by a biometric biochemical analysis system automatically detecting that the particular supplies are needed or must be replaced. Replacement may be indicated according to a level or available supply or according to other triggers such as an expiration date. These example screens illustrate directing a user to remove a BEC from the appropriate position on the biometric biochemical analysis system and to place a new or refilled BEC into the biometric biochemical analysis system. Screen 18, FIG. 4R, as described above, displays a task successfully complete indication, in this case insertion of a new BEC.

Figure 4S:
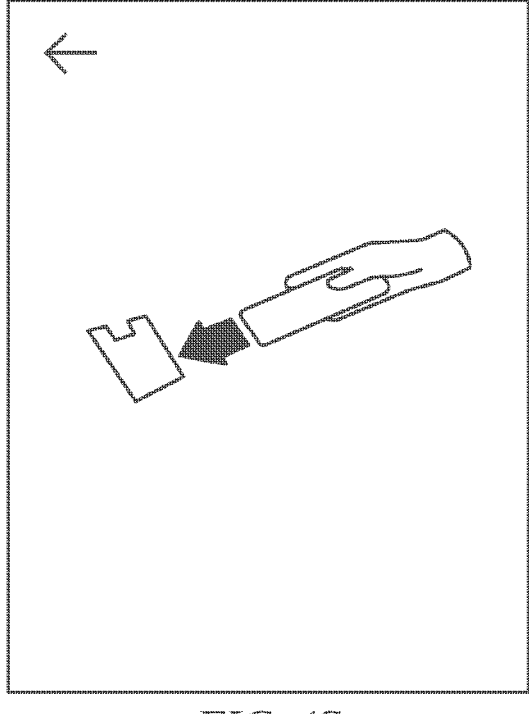
Figure 4T:
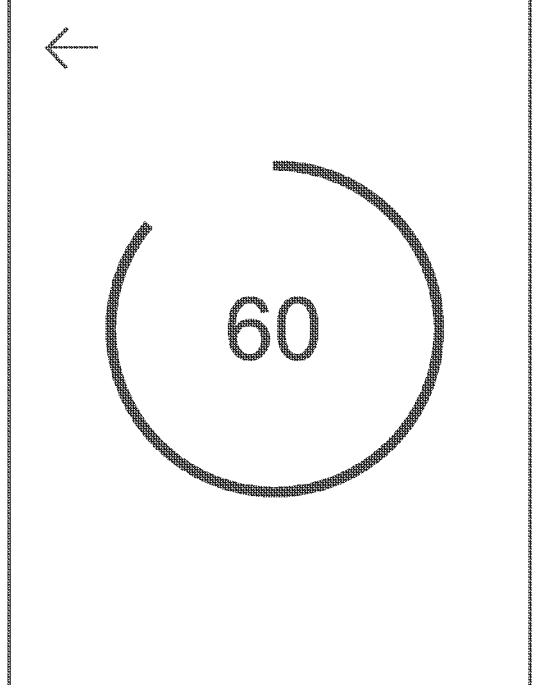
Figure 4U:
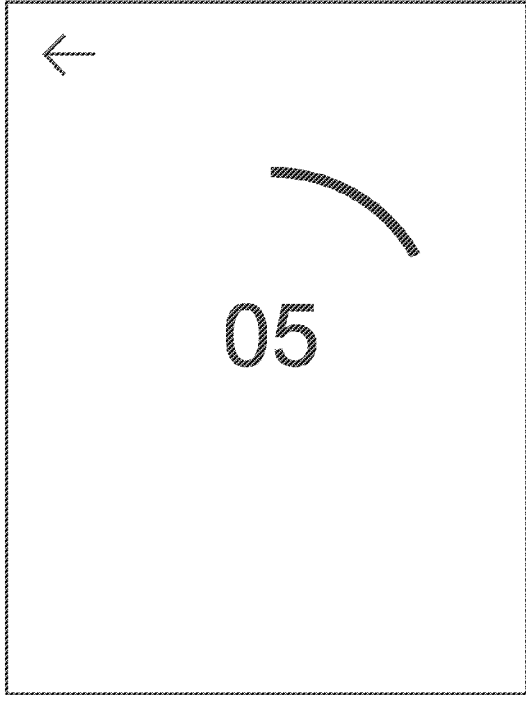
Figure 4V:
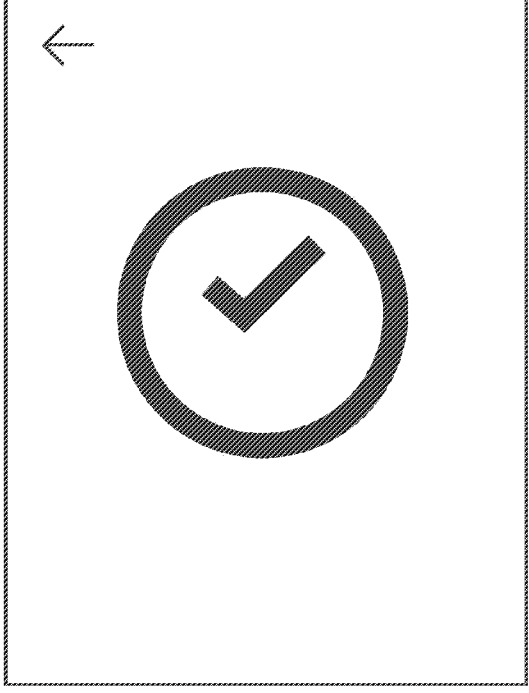
Figure 4W:
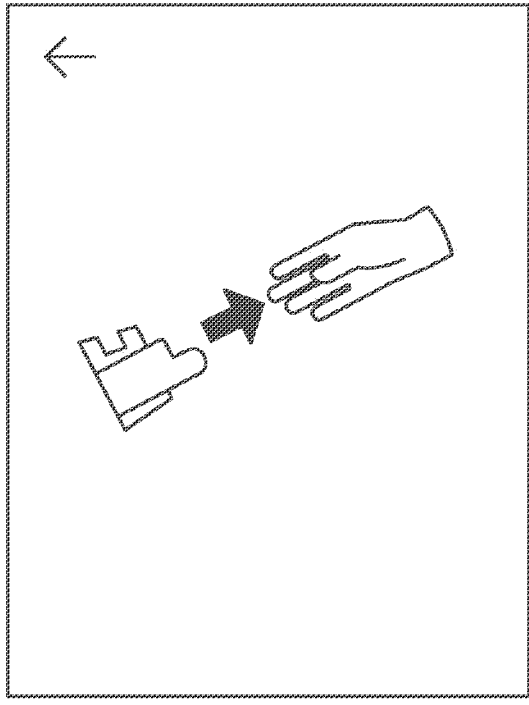
Figure 4X:
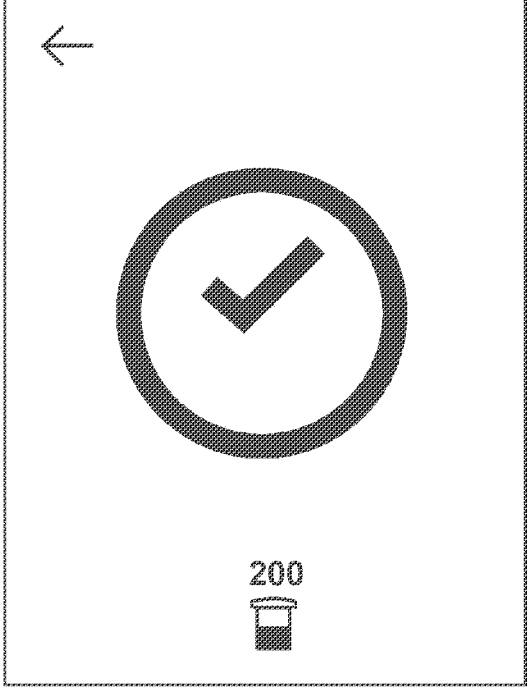

Screen 19, FIG. 4S, in this example embodiment, illustrates directing a user to place a calibration or verification sample packet into the appropriate position on the biometric biochemical analysis system. Screens 20 and 21, FIGS. 4T and 4U, in this example embodiment, illustrate a timer indicating time left for completing a calibration process. Screen 22, FIG. 4V, in this example embodiment, illustrates the system's successful completion of the calibration process. Screen 23, FIG. 4W, in this example embodiment, illustrates directing a user to remove a calibration or verification sample packet from the appropriate position on the biometric biochemical analysis system once calibration or verification is complete. Screen 24, FIG. 4X, in this example embodiment, illustrates indication of successful completion of the calibration process and that a specific number of analysis (e.g., "200") can be performed with the newly installed and calibrated BEC.

Figure 4Y:
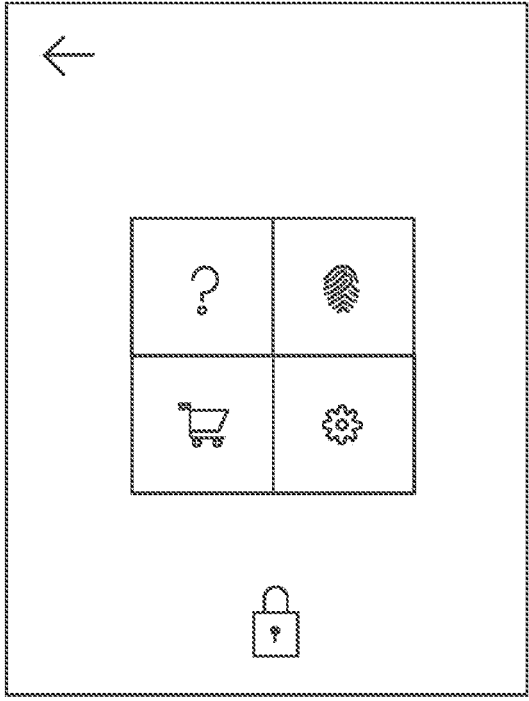
Figure 4Z:
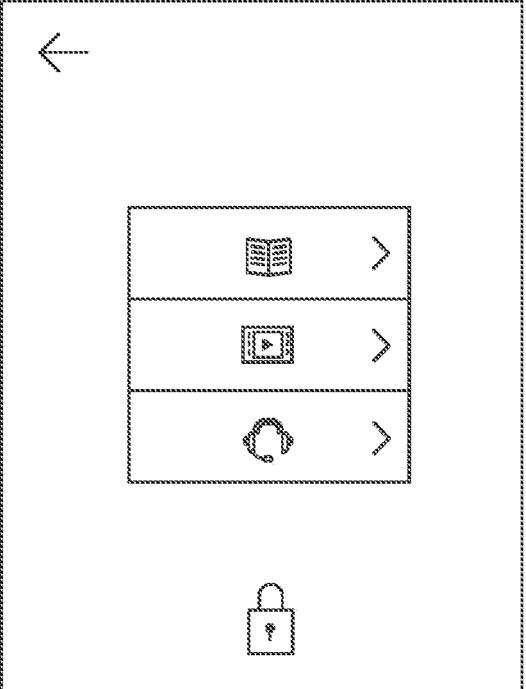
Figure 4A:
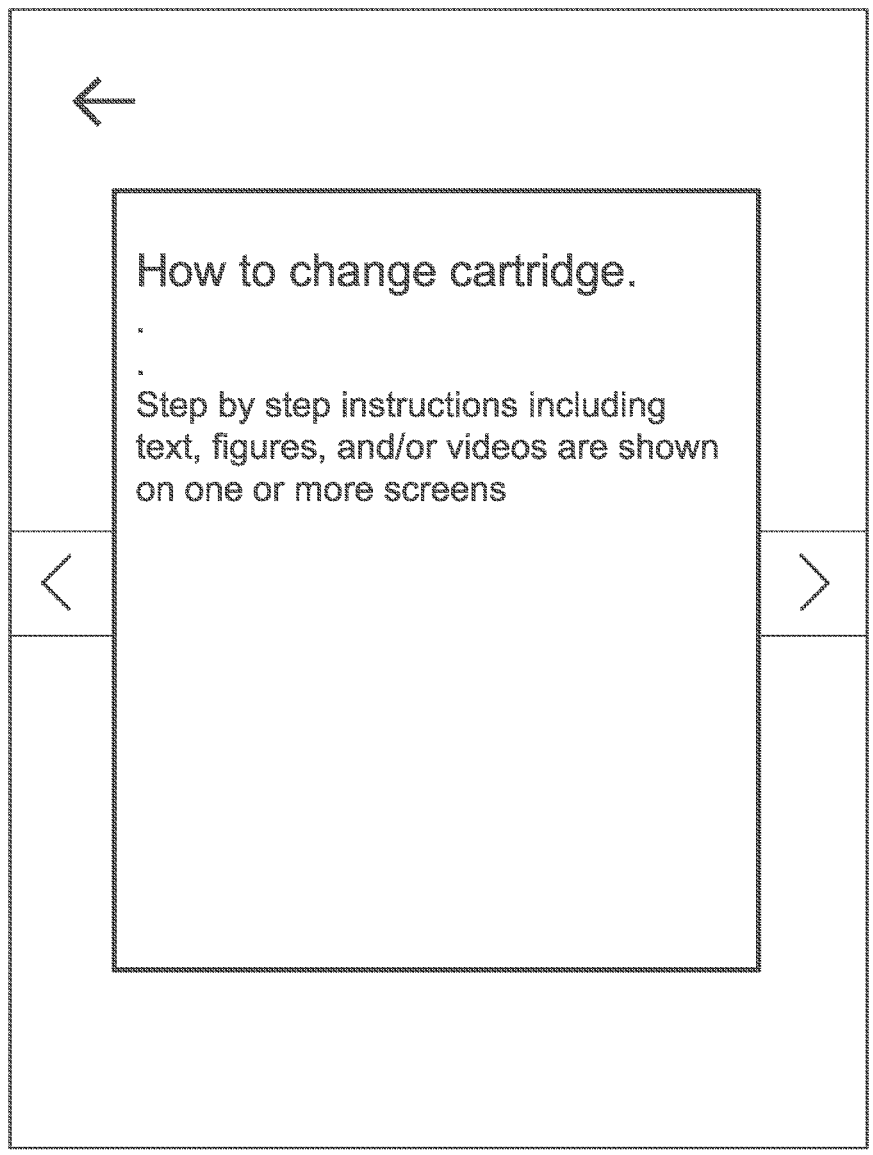
Figure 4A:
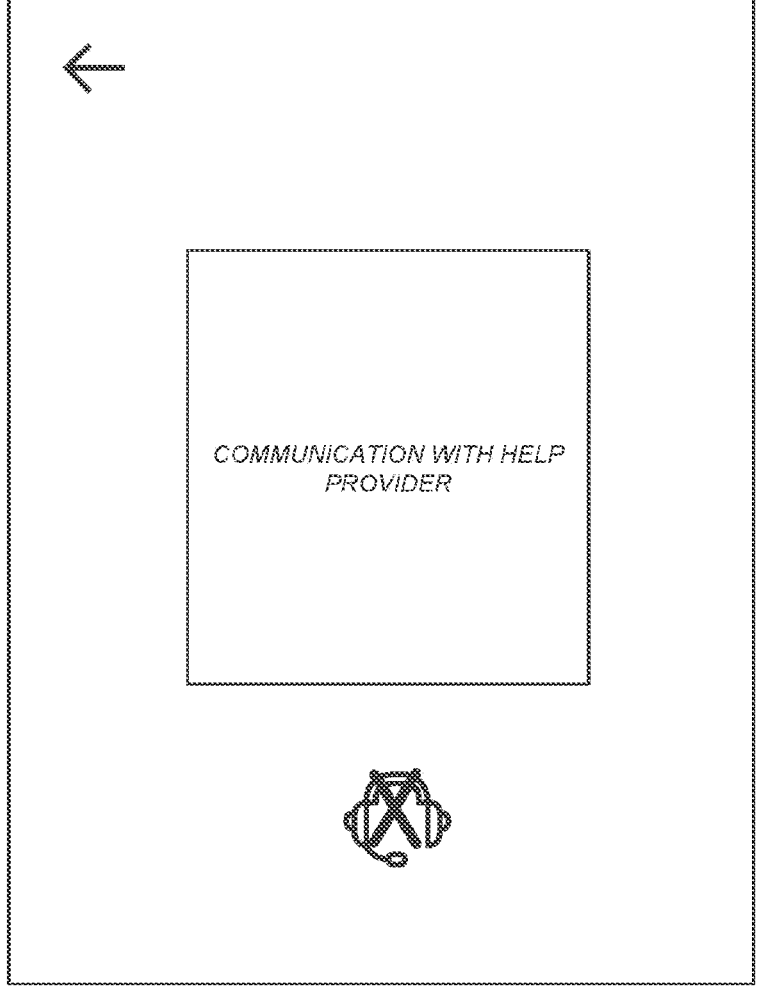

FIGS. 4Y, 4Z, 4AA and 4AB, screens 25, 26, 27, and 28, illustrate examples of menu, submenu, static help, and live help that can be provided to a user by a biometric biochemical analysis system according to specific embodiments. Example menu items shown in screen 25 include icons for help (e.g., "?" icon), returning to a login or fingerprint screen (fingerprint icon), order supplies (shopping cart icon), or setup (gear icon). Example help submenu items shown in screen 26 include icons for displaying help instructions (book icon), watching instructional or training videos (video icon), connecting to a live or automated help expert via audio or video (headset icon). Any number of further menus, options, and help functions can be provided as will be understood in the art.

While various types of assistance provided at computers and information devices are known, providing sophisticated multi-level help directly at a biometric biochemical analysis system according to specific embodiments presents novel assistance at such a device for a non-technical user. In particular, because the various components of the device are operationally and for many components physically integrated, any static context sensitive help or live help can easily determine the exact physical condition of the device and can provide assistance that activates or controls various aspects or modules of the device.

Computer Control Systems

Figure 6:
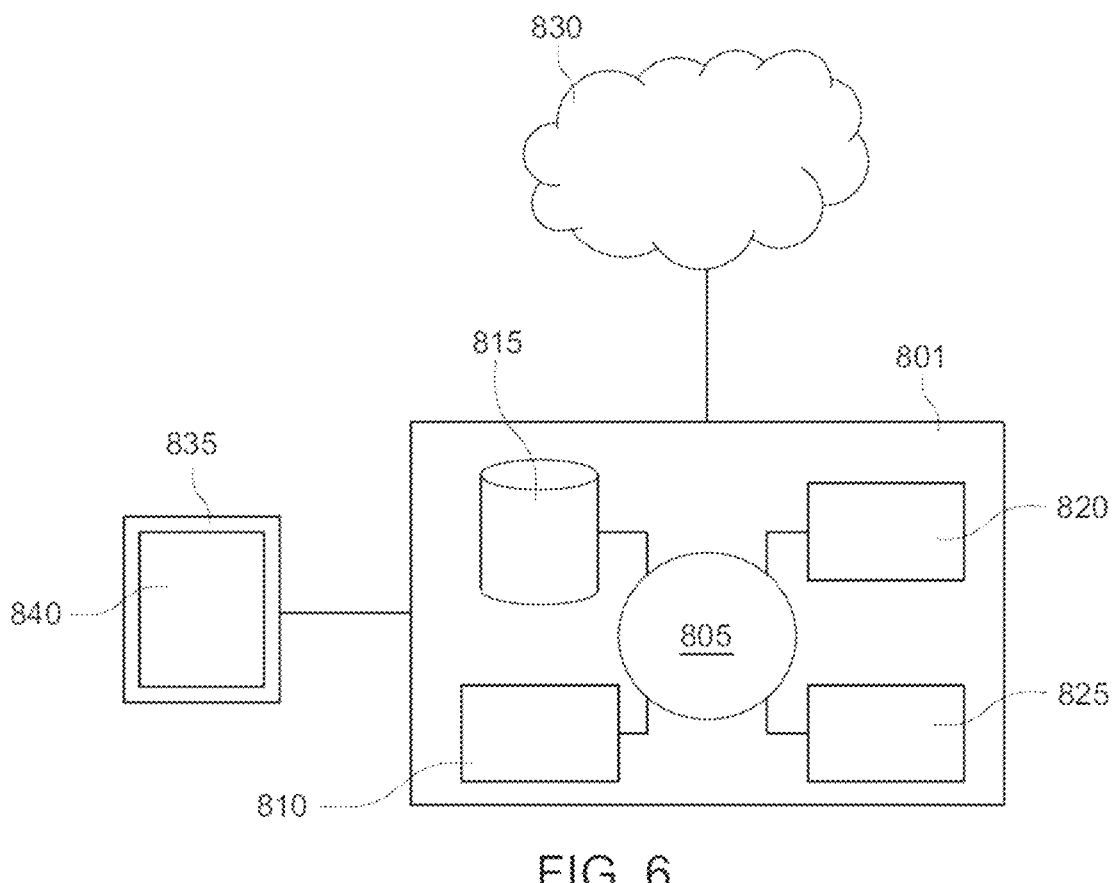
FIG. 6 shows a computer system that is programmed or otherwise configured to provide step by step user instructions for biologic sample collection and analysis and biometric data capture preparation, processing and/or analysis.

FIG. 6 shows a computer system that is programmed or otherwise configured to provide step by step user instructions for biologic sample collection and analysis and biometric data capture preparation, processing and/or analysis. FIG. 6 shows a computer system 801 that is programmed or otherwise configured to facilitate sample preparation, processing and/or analysis. The computer system 801 can regulate various aspects of sample preparation, processing and/or analysis of the present disclosure, such as, for example, engaging an electrophoresis cartridge with an electrophoresis interface of a system for sample preparation, processing and/or analysis (see, e.g., FIGS. IA-IC). The computer system 801 can be integrated with such system.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an Internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840, for example, for enabling the user to instruct the computer system 801 to begin sample preparation, processing and/or analysis. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, implement the general operation of a system for sample preparation, processing and/or analysis. In some examples, the algorithm can regulate the sequential opening and closing of valves or the operation of an electrophoresis cartridge.

Embodiment in a Programmed Information Appliance

Figure 5:
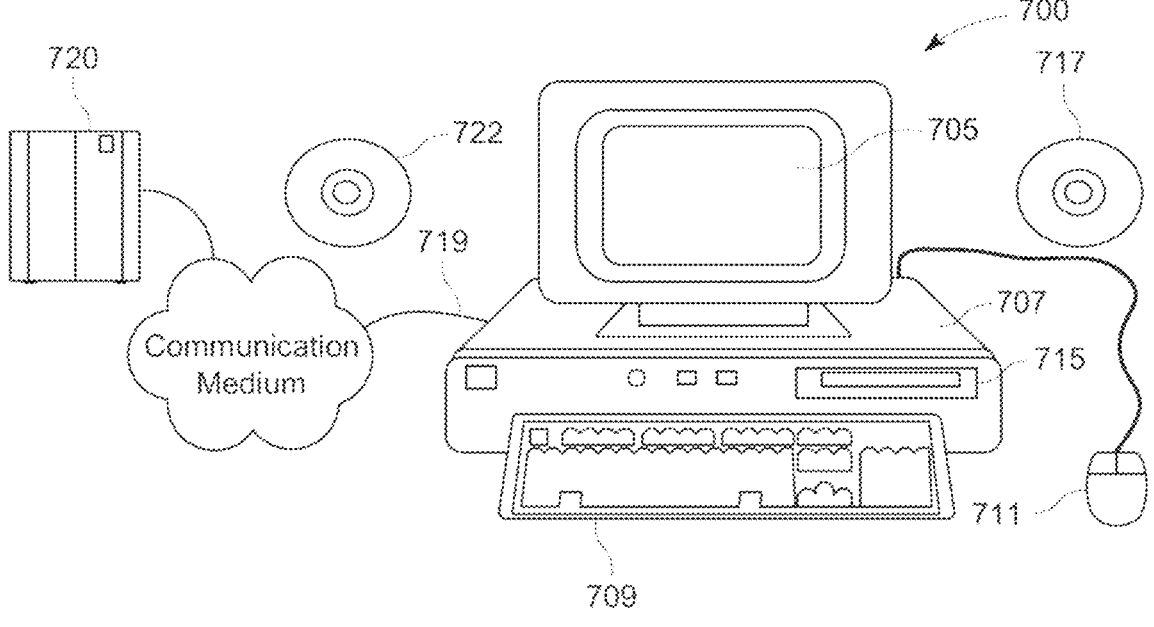
FIG. 5 is a block diagram showing a representative example logic device in which various aspects of the present invention may be embodied.

FIG. 5 is a block diagram showing a representative example logic device in which various aspects of the present invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a user on a fixed media for physically loading into a user's computer or a fixed media containing logic instructions may reside on a remote server that a user accesses through a communication medium in order to download a program component.

FIG. 5 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711; disk drives 715 and optional monitor 705. Fixed media 717, or fixed media 722 over port 719, may be used to program such a system and may represent a disk-type optical or magnetic media, mag- netic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

OTHER EMBODIMENTS

The invention has now been described with reference to specific embodiments. Other embodiments will be apparent to those of skill in the art. In particular, a user digital information appliance has generally been illustrated as a personal computer. However, the digital computing device is meant to be any information appliance for interacting with a remote data application, and could include such devices as a digitally enabled television, cell phone, personal digital assistant, laboratory or manufacturing equipment, etc. It is understood that the examples and embodiments described herein are for illustrative purposes and that various modifi- cations or changes in light thereof will be suggested by the teachings herein to persons skilled in the art and are to be included within the spirit and purview of this application and scope of the claims.

Furthermore, various different actions can be used to effect communication between a user and a biometric bio- chemical analysis system. For example, a voice command may be spoken by the user, a key or screen area may be indicated, a button or screen area on an associated module or component may be indicated, or selection using any pointing device may be effected by the user.

All publications, patents, and patent applications cited herein or filed with this application, including any references filed as part of an Information Disclosure Statement, are incorporated by reference in their entirety.

The general structure and techniques, and more specific embodiments that can be used to effect different ways of carrying out the more general goals are described herein.

Although only a few embodiments have been disclosed in detail above, other embodiments are possible and the inven- tor(s) intend these to be encompassed within this specifica- tion. The specification describes specific examples to accomplish a more general goal that may be accomplished in another way. This disclosure is intended to be exemplary, and the claims are intended to cover any modification or alternative that might be predictable to a person having ordinary skill in the art.

Also, the inventors intend that only those claims which use the words "means for" are intended to be interpreted under 35 USC 112, sixth paragraph. Moreover, no limita- tions from the specification are intended to be read into any claims, unless those limitations are expressly included in the claims. The logic components described herein may be any kind of components, either general purpose, or some specific purpose components. The component architecture may be an Intel or AMD based architecture or any other logic processing architecture. An operating system, such as Linux, Unix, Windows, etc. may be included to provide various informa- tion handling functions. One or more components may include a handheld computer, such as a PDA, cellphone, or laptop, a handheld camera, etc.

The programs may be written in C or Python, or Java, Brew or any other programming language. The programs may be resident on a storage medium, e.g., magnetic or optical, e.g., the computer hard drive, a removable disk or media such as a memory stick or SD media, wired or wireless network based or Bluetooth based Network Attached Storage (NAS), or other removable medium, or other removable medium. The programs may also be run over a network, for example, with a server or other machine sending signals to the local machine, which allows the local machine to carry out the operations described herein.

Where a specific numerical value is mentioned herein, it should be considered that the value may be increased or decreased by 20%, while still staying within the teachings of the present application, unless some different range is spe- cifically mentioned. Where a specified logical sense is used, the opposite logical sense is also intended to be encom- passed.

Software Implementations

Various embodiments involving methods and/or systems for biometric or identifying information can be implemented on a general purpose or special purpose information han- dling appliance or logic enabled system, such as a laboratory or diagnostic or production system, using a suitable pro- gramming language such as perl, python, Java, C++, C#, Cobol, C, Pascal, Fortran, PLI, LISP, assembly, etc., and any suitable data or formatting specifications, such as HTML, XML, dHTML, TIFF, JPEG, tab-delimited text, binary, etc. In the interest of clarity, not all features of an actual implementation are described in this specification. It will be understood that in the development of any such actual implementation (as in any software development project), numerous implementation-specific decisions must be made to achieve the developers' specific goals and subgoals, such as compliance with system-related and/or business-related constraints, which will vary from one implementation to another. Moreover, it will be appreciated that such a devel- opment effort might be complex and time-consuming, but would nevertheless be a routine undertaking of software engineering for those of ordinary skill having the benefit of this disclosure.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innova- tive combinations of innovative components and known components. No inference should be taken to limit the invention to combinations containing all of the innovative components listed in any illustrative embodiment in this specification.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descrip- tions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system, comprising:
an authentication sub-system comprising a processor configured to receive input from a user and authenticate the user based on the input; and
a biochemical analysis sub-system configured to receive a biological sample and to perform a biochemical analysis on the received biological sample,
wherein, in response to authentication of a user by the authentication sub-system, the system is configured to:
instruct the user to provide a biological sample to the biochemical analysis sub-system;
automatically cause the biochemical analysis sub-system to execute a biochemical analysis on a biological sample to produce biometric data;
communicate the biometric data to a criminal records database; and
receive information from the criminal records database regarding whether or not the biometric data matches one or more records in the criminal records database.

2. The system of claim 1, wherein the biometric data comprise genetic data.

3. The system of claim 1, wherein the criminal records database is remote from the authentication sub-system.

4. The system of claim 1, wherein the biochemical analysis sub-system is configured to perform electrophoresis.

5. The system of claim 1, further comprising:
a digital biometric data capture device, wherein the system is further configured to, in response to authentication of the user, instruct the user to electronically capture biometric data from a source of the biological sample using the digital biometric data capture device.

6. The system of claim 5, wherein the digital biometric data capture device comprises one or more of a camera, a fingerprint reader, or a retinal scanner.

7. A method, comprising:
authenticating a user by an authentication sub-system comprising a processor configured to receive input from a user and to authenticate the user based on the input;
in response to authenticating the user, instruct the user to input a biological sample to a biochemical analysis sub-system;
using the biochemical analysis sub-system, performing a biochemical analysis on a biological sample input by the user to produce biometric data;
communicating the biometric data from the biochemical analysis sub-system to a criminal records database; and
receiving information from the criminal records database regarding whether or not the biometric data matches one or more records in the criminal records database.

8. The method of claim 7, wherein performing the biochemical analysis comprises performing electrophoresis.

9. The method of claim 7, wherein performing the biochemical analysis comprises performing a biochemical reaction on an analyte in the biological sample to produce a reaction product and detecting the reaction product.

10. The method of claim 7, further comprising:
capturing additional biometric data from a source of the biological sample using a digital biometric data capture device.

11. The method of claim 10, wherein the digital biometric data capture device comprises a camera, a fingerprint reader, or a retinal scanner.

12. The method of claim 7, wherein the biometric data is genetic data.

13. A system, comprising:
a processor;
a digital biometric data capture module;
a biochemical analyzer module configured to receive and perform a biochemical analysis of a biological sample and produce biometric data based on the biochemical analysis;
a communications interface; and
a user interface;
wherein the processor is configured with instructions which upon execution cause the system to:
direct a user, via the user interface, capture biometric data of a third party using the digital biometric data capture module,
communicate the captured biometric data via the communications interface to a remote database, and
based on a comparison of the captured biometric data with data stored in the remote database, provide output at the user interface to the user.

14. The system of claim 13, wherein the output comprises an indication the database comprises data corresponding to biometric data of the third party.

15. The system of claim 13, wherein the output comprises an indication the biometric data of the third party does not correspond to data contained in the database.

16. The system of claim 15, wherein the processor is further configured with instructions which upon execution cause the system to:
after outputting the indication at the user interface, direct the user, via the user interface, to input a biological sample from the third party to the biochemical analyzer module.

17. The system of claim 16, wherein the processor is further configured with instructions which upon execution cause the biochemical analyzer module to perform a biochemical analysis of the input biological sample and produce additional biometric data based on the biochemical analysis.

18. The system of claim 17, wherein the processor is further configured with instructions which upon execution cause the system to communicate, via the communications interface, the additional biometric data from the biochemical analyzer module to the remote database.

19. The system of claim 13, wherein the output at the user interface comprises:
directions to the user to perform analysis of a biological sample from the third party using the biochemical analyzer module in response to the captured biometric data not matching data stored in the remote database based on the comparison, or confirmation to the user of the captured biometric data matching data stored in the remote database based on the comparison.

\* \* \* \* \*